US010112003B2

(12) United States Patent
Kimura

(10) Patent No.: US 10,112,003 B2
(45) Date of Patent: *Oct. 30, 2018

(54) BLOOD COMPONENT SEPARATION DEVICE

(71) Applicant: TERUMO KABUSHIKI KAISHA, Tokyo (JP)

(72) Inventor: Shigeyuki Kimura, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/497,494

(22) Filed: Apr. 26, 2017

(65) Prior Publication Data

US 2017/0224905 A1 Aug. 10, 2017

Related U.S. Application Data

(60) Division of application No. 14/481,503, filed on Sep. 9, 2014, which is a continuation of application No. PCT/JP2013/054841, filed on Feb. 26, 2013.

(30) Foreign Application Priority Data

Mar. 27, 2012 (JP) ................................ 2012-072505

(51) Int. Cl.
*A61M 1/36* (2006.01)
*A61M 1/38* (2006.01)
(Continued)

(52) U.S. Cl.
CPC ........ *A61M 1/3696* (2014.02); *A61M 1/0218* (2014.02); *A61M 1/382* (2013.01);
(Continued)

(58) Field of Classification Search
CPC .. A61M 1/3696; A61M 1/382; A61M 1/0231; A61M 1/0218; A61M 1/3693;
(Continued)

(56) References Cited

U.S. PATENT DOCUMENTS 5,939,319 A 8/1999 Hlavinka et al.
6,743,192 B1 6/2004 Sakota et al.
(Continued)

FOREIGN PATENT DOCUMENTS

JP 2000084066 A 3/2000
JP 2003088581 A 3/2003
(Continued)

OTHER PUBLICATIONS

English translation of International Search Report for PCT Application No. PCT/2012/073199, Japanese Patent Office, dated Dec. 11, 2012, p. 1-2.
(Continued)

*Primary Examiner* — Timothy C Cleveland
(74) *Attorney, Agent, or Firm* — John R. Merkling

(57) ABSTRACT

A blood component separation device includes a centrifuge bowl for separating a blood component from blood, a plasma bag for storing a plasma component, a platelet intermediate bag for storing high-concentration platelet liquid having high-concentration of platelets, and a temporary storage bag (also used as a buffy coat bag) for storing low-concentration platelet liquid having low-concentration of platelets. The blood component separation device performs control, from the second cycle onward, to mix the low-concentration platelet liquid stored in the temporary storage bag in the immediately preceding cycle with whole blood to supply the mixed liquid to the centrifuge bowl. An amount of high-concentration platelet liquid to be collected in the platelet intermediate bag in the first cycle is set to be smallest among all cycles, and an amount of high-concentration platelet liquid to be collected in a last cycle is set to be greatest among all the cycles.

3 Claims, 20 Drawing Sheets

(51) Int. Cl.
*A61M 1/02* (2006.01)
*B04B 11/02* (2006.01)
*B04B 5/04* (2006.01)

(52) U.S. Cl.
CPC ............ *B04B 5/0442* (2013.01); *B04B 11/02* (2013.01); *A61M 2202/0427* (2013.01)

(58) Field of Classification Search
CPC ......... A61M 2202/0427; B04B 5/0442; B04B 11/00; B04B 11/02; B04B 11/04
See application file for complete search history.

(56) References Cited

U.S. PATENT DOCUMENTS

| | | | |
|---|---|---|---|
| 7,413,665 | B2 | 8/2008 | Holmes et al. |
| 9,452,254 | B2 | 9/2016 | Kimura et al. |
| 9,669,152 | B2 * | 6/2017 | Kimura ............... A61M 1/3693 |
| 2003/0066807 | A1 | 4/2003 | Suzuki |
| 2015/0011371 | A1 | 1/2015 | Kimura et al. |
| 2015/0231315 | A1 | 8/2015 | Kimura |
| 2015/0367063 | A1 | 12/2015 | Kimura |

FOREIGN PATENT DOCUMENTS

| | | |
|---|---|---|
| JP | 2003516175 A | 5/2003 |
| JP | 2004358041 | 12/2004 |
| JP | 2004358041 A | 12/2004 |
| JP | 2005296675 A | 10/2005 |
| JP | 2006051252 A | 2/2006 |
| JP | 2009226210 A | 10/2009 |
| JP | 2012081213 A | 4/2012 |
| WO | WO2001028621 A1 | 5/2003 |
| WO | WO2008056733 A1 | 5/2008 |
| WO | WO2013145997 A1 | 10/2013 |
| WO | WO2013146010 A1 | 10/2013 |
| WO | WO2014041600 A1 | 3/2014 |
| WO | WO2014102888 A1 | 7/2014 |
| WO | WO2014132327 A1 | 9/2014 |
| WO | WO2016043003 A1 | 3/2016 |

OTHER PUBLICATIONS

English Translation of the International Written Opinion and Preliminary Report on Patentability for PCT Application No. PCT/JP2012/073199, dated Mar. 26, 2015, performed by the International Bureau of WIPO, 12 pages, Geneva Switzerland.
International Search report for PCT Application No. PCT/JP2013/054841, issued by the Japanese Patent Office dated May 21, 2013.

* cited by examiner

Fig.20

| | 1cyc | 2cyc | 3cyc | 4cyc | Total |
|---|---|---|---|---|---|
| Embodiment 1 | 20ml | 20ml | 20ml | 40ml | 100ml |
| Embodiment 2 | 20ml | 24ml | 28ml | 28ml | 100ml |
| Embodiment 3 | 20ml | 22ml | 26ml | 32ml | 100ml |

BLOOD COMPONENT SEPARATION DEVICE

CROSS REFERENCE TO RELATED APPLICATIONS

This application is a division of U.S. application Ser. No. 14/481,503, filed Sep. 9, 2014, which is a continuation of PCT/JP2013/054841, filed Feb. 26, 2013, which claims the benefit of Japanese Patent Application No. 2012-072505, filed Mar. 27, 2012.

TECHNICAL FIELD

The present invention relates to a blood component separation device for collecting platelets from blood. More specifically, the present invention relates to a blood component separation device performing concentration and collection of platelets.

BACKGROUND ART

Conventionally, in the field of blood drawing, a blood component such as platelets is collected by collecting only the component from drawn blood and returning the remaining blood components into the donor. In such operation, a blood component separation device including a centrifugal separator is used.

In recent years, in the field of radiation therapy of cancer or the like, transfusion of platelets is widely performed, and high-concentration platelet liquid is necessary. To obtain high-concentration platelet liquid, Patent Literature 1 discloses an art using a blood component separation device to temporarily store low-concentration platelet liquid in a buffy coat bag and store only high-concentration platelet liquid in a platelet intermediate bag.

In this operation, low-concentration platelet liquid flows out first from the centrifugal separator, then high-concentration platelet liquid, and finally low-concentration platelet liquid again. When the first portion and the last portion of the platelet liquid, which has low-concentration of platelets, are stored in the platelet intermediate bag, the concentration of the platelet liquid stored in the platelet intermediate bag will naturally be reduced.

To avoid such reduction in concentration, the low-concentration platelet liquid, that is, the first portion and the last portion of the platelet liquid, is temporarily stored in the buffy coat bag. In the second cycle, the stored platelet liquid is mixed with the whole blood drawn from a donor and supplied to the centrifugal separator. By repeating this process, only high-concentration platelet liquid can be stored in the platelet intermediate bag.

CITATION LIST

Patent Literature

Patent Literature 1: JP 2009-226210 A

SUMMARY OF INVENTION

Technical Problem

In the blood component separation device mentioned above, the high-concentration platelet liquid is collected for each cycle (amount to be collected is almost the same for each cycle) based on concentration of the platelet liquid (value from the line sensor) flowing out from the centrifugal separator. The target amount is collected by repeating the collection for a predetermined number of cycles. The platelet concentration in the centrifugal separator is the highest in the last cycle.

However, the blood component separation device mentioned above has disadvantage that collection of platelets is not efficient since the amount of high-concentration platelet liquid collected in the last cycle is the same as that of other cycles.

The present invention is made to solve the problem. The object of the present invention is to provide a blood component separation device that can efficiently collect greater amount of platelets.

Solution to Problem

To solve the problem described above, an aspect of the present invention is a blood component separation device including a centrifugal separator for separating a predetermined blood component from blood and a container for containing the predetermined blood component which is centrifugally separated. The blood component separation device is configured to perform (a) centrifugal separation step for introducing the whole blood drawn from a donor into the centrifugal separator to separate the whole blood into a plurality of blood components, (b) circulation flow step for introducing a predetermined first blood component, among centrifugally separated blood components, separated by the centrifugal separation into the centrifugal separator together with whole blood, (c) circulation/acceleration step, performed after a predetermined amount of the first blood component is separated in the circulation flow step, in which the supply of whole blood to the centrifugal separator is stopped to introduce only the first blood component into the centrifugal separator to further circulate the first blood component for a predetermined period of time, and a circulation speed is then increased so that a second blood component is separated by the centrifugal separator and collected, and (d) blood returning step for returning blood components remaining after collecting a predetermined amount of the second blood component in the circulation/acceleration step to the donor. The circulation/acceleration step includes a first collecting step for transferring a portion of the second blood component with low-concentration to a temporary storage container and a second collecting step for collecting a portion of the second blood component with high-concentration. The second blood component with low-concentration transferred to the temporary storage container is introduced into the centrifugal separator together with the whole blood drawn in the following cycle, where the steps (a) to (d) constitute one cycle. As for the second collecting step, the amount of the second blood component with high-concentration to be collected in the first cycle is set to be the smallest among all cycles, and the amount of the second blood component with high-concentration to be collected in the last cycle is set to be the greatest among all the cycles.

The minimum amount to be collected set for the first cycle may be same as the amount to be collected set for other cycles. Similarly, the maximum amount to be collected set for the last cycle may be same as the amount to be collected set for other cycles.

In the blood component separation device, from the second cycle onward, the second blood component with low-concentration stored in the temporary storage container in the immediately preceding cycle is mixed with the whole blood drawn in the present cycle and supplied to the centrifugal separator, so that the concentration of the second blood component in the centrifugal separator gradually rises and become greatest at the last cycle.

Further, the amount of the second blood component with high-concentration collected in the first cycle is set to be the smallest among all the cycles, and the amount of the second blood component with high-concentration collected in the last cycle is set to be the greatest among all the cycles. Therefore, for the same target amount (total amount) of the second blood component with high-concentration to be collected, greater amount of the second blood component can be collected than a conventional device. Consequently, the blood component separation device can efficiently collect greater amount of the second blood component.

The blood component separation device described above may be configured to vary the amount of the second blood component with high-concentration to be collected in the second collecting step for each cycle.

In this case, it is preferable to vary the amount of the second blood component with high-concentration to be collected in the second collecting step for each step so as that the amount to be collected in each cycle shall not be smaller than the amount collected in the preceding cycle.

By varying the amount of the second blood component with high-concentration to be collected in each cycle so as not to be smaller than the amount collected in the preceding cycle, the second blood component with high-concentration can efficiently be collected not only in the last cycle but also in other cycles. As a result, the second blood component can further efficiently be collected.

Further, the blood component separation device described above may include a whole blood bag to store the whole blood drawn from a donor, and be configured to introduce the whole blood stored in the whole blood bag into the centrifugal separator, in the centrifugal separation step in the following cycle, together with the whole blood drawn in the following cycle.

In this manner, whole blood can be drawn from the donor in parallel with performing at least one of the circulation flow step and the acceleration step in the first cycle (present cycle). Therefore, in addition to the effect described above, the time required to draw whole blood in the second cycle (following cycle) can be reduced, thereby reducing the time required for the entire process. This reduces the time in which the donor receives stress.

For example, typical time periods in each cycle are about 9 minutes for the blood drawing and the circulation flow step (critical flow step), 30 to 40 seconds for the circulation step in the circulation/acceleration step, 20 to 30 seconds for the acceleration step in the circulation/acceleration step, and about 4 minutes for the blood returning. According to the present invention, since blood is previously drawn for one minute in the first cycle, the time required to draw blood in the second cycle can be reduced by one minute, that is, to about eight minutes. Similarly, when total three cycles are performed, the time required to draw blood in the third cycle can be reduced by one minute, that is, to about eight minutes.

There is a problem for a donor that the amount of blood circulating outside the body increases, although it may not be a problem for 90% of donors. If there may be a problem in increasing the amount of blood circulating outside the body according to the result of previous check, a switching unit may be used to avoid drawing whole blood in parallel with the circulation/acceleration step in the first cycle (present cycle), and to draw whole blood in the second cycle (following cycle) after returning blood. It goes without saying that, in the last cycle, whole blood is not drawn for the following cycle because there is no cycle following the last cycle.

In this case, the whole blood bag may preferably be used as a temporary storage container.

Therefore, no additional whole blood bag is required, so that the device need not be large and there is no need to specially prepare a disposable whole blood bag. This can reduce cost.

Further, it is preferable to further include a pump to introduce the whole blood or/and the second blood component stored in the temporary storage container in the preceding cycle into the centrifugal separator in the centrifugal separation step in the following cycle.

In this manner, the whole blood or/and the second blood component with low-concentration stored in the preceding cycle can surely be introduced into the centrifugal separator without delay.

Advantageous Effects of Invention

The blood component separation device having such configuration can efficiently collect greater amount of platelets as described above.

BRIEF DESCRIPTION OF DRAWINGS

FIG. 20 shows a collected amount of platelet liquid in each cycle.

DESCRIPTION OF EMBODIMENTS

Figure 1:
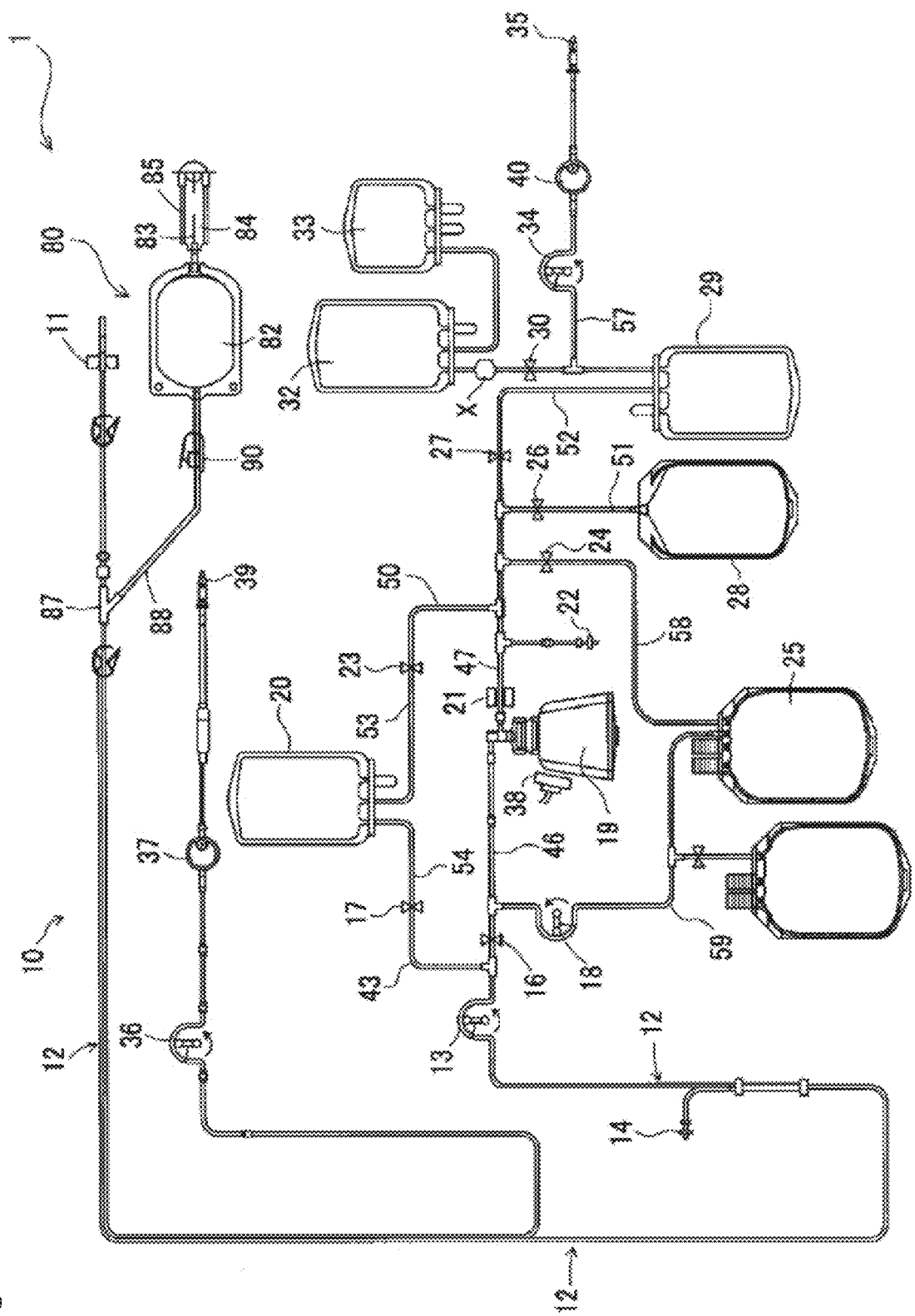
FIG. 1 illustrates a configuration of a blood component separation device according to an embodiment.
Figure 2:
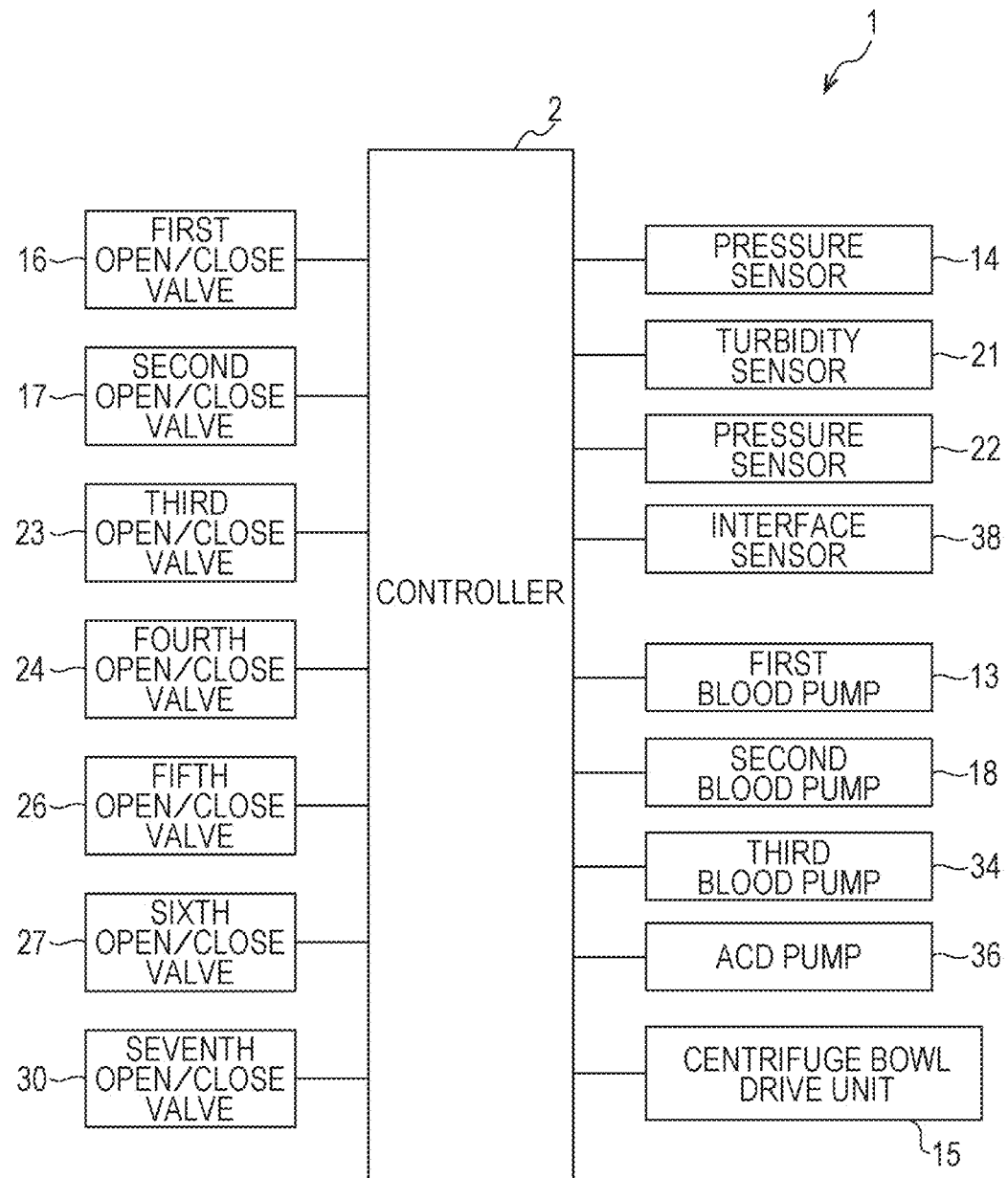
FIG. 2 is a block diagram illustrating a control system of the blood component separation device according to the embodiment.
Figure 3:
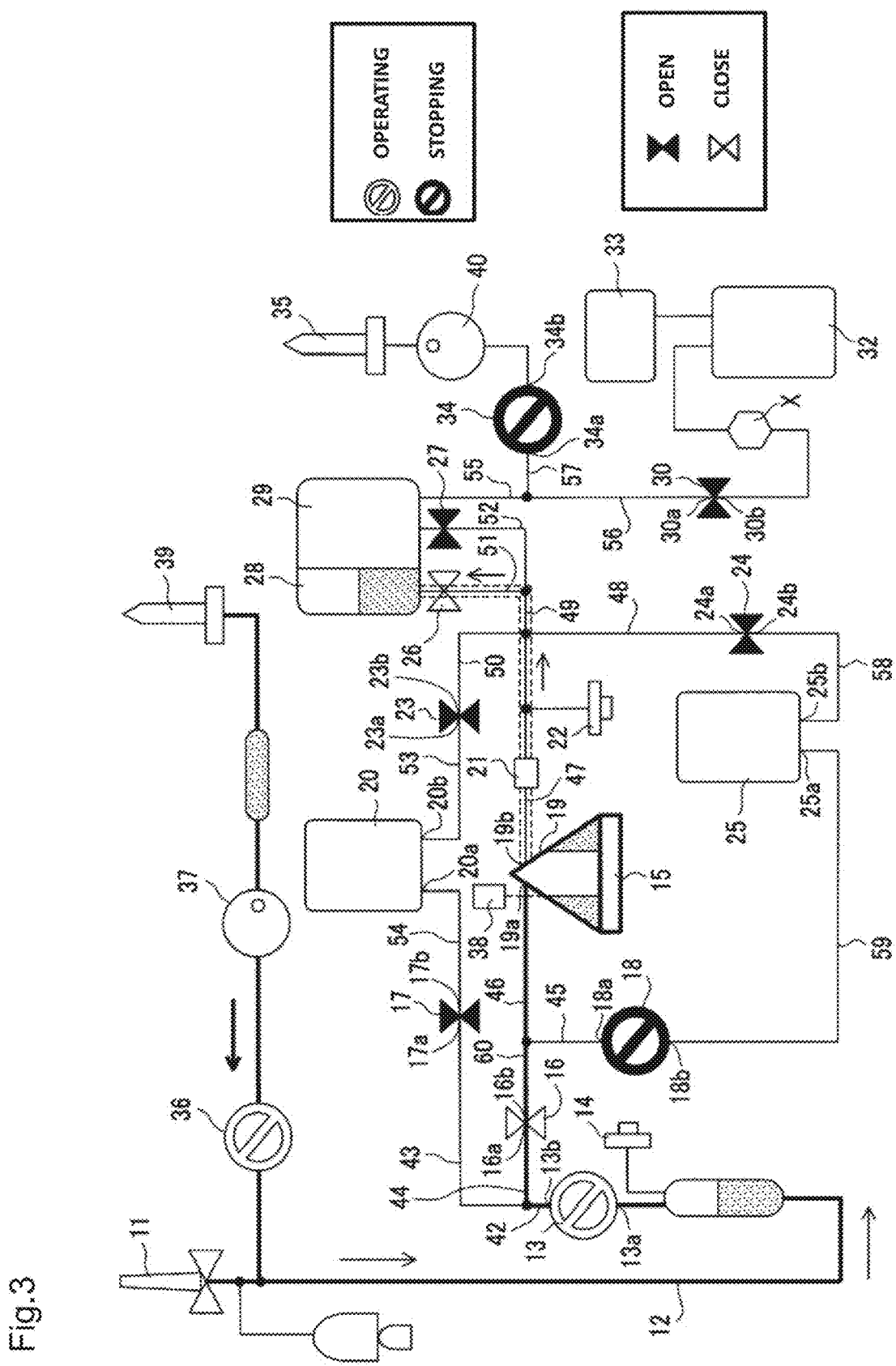
FIG. 3 is a drawing for explaining a first step (priming step) of the blood component separation device according to the embodiment.

An embodiment of a blood component separation device according to the present invention will be described in detail below referring to the drawings. First, a system configuration of the blood component separation device according to the embodiment will be described referring to FIGS. 1 to 3. FIG. 1 illustrates a configuration of the blood component separation device according to the embodiment. FIG. 2 is a block diagram illustrating a control system of the blood component separation device according to the embodiment. FIG. 3 is a drawing for explaining a first step (priming step) of the blood component separation device according to the embodiment.

As illustrated in FIGS. 1 to 3, a blood component separation device 1 according to the embodiment includes a blood component separation circuit 10. The blood component separation circuit 10 includes a blood drawing needle 11, an initial blood flow collecting circuit 80 configured with an initial blood flow collecting bag 82 for collecting initial blood flow, a sampling port 85, and an initial blood flow collecting line 88, a centrifuge bowl 19 including a rotor having therein a space for storing drawn blood, a centrifuge bowl drive unit 15 for driving the rotor, an inflow port (first port 19a), and an outflow port (second port 19b), and configured to separate blood into a plurality of blood components by rotating the rotor, three containers, that is, a first container (plasma bag) 25, a second container (temporary storage bag) 20, and a third container (platelet intermediate bag) 29 each of which storing blood components separated by the centrifuge bowl 19, a first line (a donor tube 12, a first blood pump 13, a tube 42, a tube 44, a first open/close valve 16, a tube 60, and a tube 46) coupling the blood drawing needle 11 to the centrifuge bowl 19, a second line (a tube 47, a tube 48, a fourth open/close valve 24, and a tube 58) coupling the centrifuge bowl 19 to the first container 25, a third line (a tube 59, a second blood pump 18, and a tube 45) coupling the first container 25 to the first line, a fourth line (a tube 47, a tube 50, a third open/close valve 23, and a tube 53) coupling the centrifuge bowl 19 to the second container 20, a fifth line (a tube 54, a second open/close valve 17, and a tube 43) coupling the second container 20 to the first line, and a sixth line (a tube 47, a tube 49, a tube 52, and a sixth open/close valve 27) coupling the centrifuge bowl 19 to the third container 29.

The blood drawing needle 11, which is a collecting unit to collect whole blood (blood) from a donor, is coupled to a first port 13a of the first blood pump 13 via the donor tube 12. The initial blood flow collecting bag 82 is coupled to the blood drawing needle via a branch provided on the donor tube 12 and the initial blood flow collecting line 88. The initial blood flow collecting bag 82 further includes a sampling port 85 for transferring collected initial blood flow to a test container (not shown). The sampling port 85 is constituted with a main body, a needle 83, and a cover 84 for covering the needle. Further, a klemme 90 is provided on the initial blood flow collecting line to open/close the line.

The tube 42 coupled to a second port 13b of the first blood pump 13 is branched into two tubes 43 and 44. The tube 44 is coupled to a first port 16a of the first open/close valve 16. The tube 60 coupled to a second port 16b of the first open/close valve 16 is branched into two tubes 45 and 46. The tube 46 is coupled to the first port 19a of the centrifuge bowl 19 which is a centrifugal separator for separating the drawn blood into a plurality of blood components. The centrifuge bowl 19 is arranged on the centrifuge bowl drive unit 15 to be rotatably driven.

The blood drawing needle 11 and the first port 19a, which is an inlet to the centrifuge bowl 19, are coupled via the first line (the donor tube 12, the first blood pump 13, the tube 42, the tube 44, the first open/close valve 16, the tube 60, and the tube 46). A pressure sensor 14 is coupled to the donor tube 12.

The tube 47 coupled to the second port 19b of the centrifuge bowl 19 is branched into three tubes 48, 49 and 50. The tube 48 is coupled to an input port 24a of the fourth open/close valve 24. An output port 24b of the fourth open/close valve 24 is coupled to an input port 25b of the plasma bag (first container) 25 via the tube 58.

The second port 19b, which is an outlet from the centrifuge bowl 19, and the plasma bag 25 are coupled via the second line (the tube 47, the tube 48, the fourth open/close valve 24, and the tube 58). An output port 25a of the plasma bag 25 is coupled to an input port 18b of the second blood pump 18 via the tube 59.

The plasma bag 25 is coupled to the tubes 46 and 60, constituting the first line, via the tube 45. That is, the plasma bag 25 and the first line are coupled via the third line (the tube 59, the second blood pump 18, and the tube 45). In this manner, the plasma bag 25 is coupled so as to selectively communicate with the inlet to or the outlet from the centrifuge bowl 19.

An air bag for temporarily storing air in the circuit is coupled to the tube 59 (between the first container 25 and the second blood pump 18) of the third line (see FIG. 1).

The tube 50 branched from the tube 47 is coupled to a second port 23b of the third open/close valve 23. A first port 23a of the third open/close valve 23 is coupled to a second port 20b of the temporary storage bag 20 via the tube 53. That is, the second port 19b of the centrifuge bowl 19 and the temporary storage bag 20 are coupled via the fourth line (the tube 47, the tube 50, the third open/close valve 23, and the tube 53).

A first port 20a of the temporary storage bag 20 is coupled to a second port 17b of the second open/close valve 17 via the tube 54. A first port 17a of the second open/close valve 17 is coupled to the tube 42 via the tube 43. That is, the temporary storage bag 20 and the tube 42 are coupled via the fifth line (the tube 43, the second open/close valve 17, and the tube 54). In this manner, the temporary storage bag 20 is coupled so as to selectively communicate with the inlet to or the outlet from the centrifuge bowl 19.

The tube 49 is further branched into tubes 51 and 52. The tube 51 is coupled to the air bag 28 via the fifth open/close valve 26, and the tube 52 is coupled to the platelet intermediate bag (third container) 29 via the sixth open/close valve. That is, the second port 19b of the centrifuge bowl 19 and the platelet intermediate bag 29 are coupled via the sixth line (the tube 47, the tube 49, the tube 52, and the sixth open/close valve 27). In this manner, the platelet intermediate bag 29 selectively communicates with the inlet to or the outlet from the centrifuge bowl 19.

A turbidity sensor 21 for detecting concentration of platelets and a pressure sensor 22 are attached to the tube 47 coupled to the second port 19b of the centrifuge bowl 19. The turbidity sensor 21 detects the turbidity, made by platelets, of plasma flowing in the tube 47. In the peripheral region of where the centrifuge bowl 19 is attached, an interface sensor 38 for detecting the location of the interface of buffy coat layer BC formed in the centrifuge bowl 19 is provided.

The tube 55 coupled to the platelet intermediate bag 29 is branched into two tubes 56 and 57. The tube 56 is coupled to an inlet port 30a of the seventh open/close valve 30, and the tube 57 is coupled to an outlet port 34a of the third blood pump 34. An inlet port 34b of the third blood pump 34 is coupled to a platelet reserve liquid bottle via a sterilizing filter 40 and a bottle needle 35. An outlet port 30b of the seventh open/close valve 30 is coupled to the platelet bag 32 via a white blood cell removal filter X. Further, an air bag 33 is coupled to the platelet bag 32.

An output port of an ACD pump 36 is coupled to the donor tube 12. An input port of the ACD pump 36 is coupled to an output port of the sterilizing filter 37. An input port of the sterilizing filter 37 is coupled to an ACD storing bottle via a bottle needle 39.

As illustrated in FIG. 2, a controller 2 is configured with, for example, a microcomputer. The controller 2 is electrically coupled to the first blood pump 13, the second blood pump 18, the third blood pump 34, the centrifuge bowl drive unit 15, the ACD pump 36, the turbidity sensor 21, the interface sensor 38, the pressure sensors 14 and 22, the first open/close valve 16, the second open/close valve 17, the third open/close valve 23, the fourth open/close valve 24, the fifth open/close valve 26, the sixth open/close valve 27, and the seventh open/close valve 30.

Detection signals from the sensors 14, 21, 22, and 38 are input to the controller 2 as required. Based on these detection signals or the like, the controller 2 operates or stops the pumps 13, 18, 34, and 36 and controls rotational directions (normal rotation/reverse rotation) and rotational speeds of the pumps. The controller 2 also opens or closes the open/close valves 16, 17, 23, 24, 26, 27, and 30 or controls the operation of the centrifuge bowl drive unit 15 as required.

As a material of the tubes, for example, thermoplastic elastomers such as polyvinyl chloride, polyethylene, polypropylene, polyester such as PET and PBT, ethylene-vinyl acetate copolymer (EVA), polyurethane, and polyester elastomer may be used. Among these materials, particularly, polyvinyl chloride is preferably used. Polyvinyl chloride not only has sufficient ductility and flexibility but also is easy to handle and suitable to be choked by a klemme or the like.

As a material of the bags, soft polyvinyl chloride including DEHP as a plasticizer or products of polymerization or copolymerization of such olefins or diolefins as polyolefin, ethylene, propylene, butadiene, and isoprene can be used. Typical examples include ethylene-vinyl acetate copolymer (EVA), polymer blends formed between EVA and various thermoplastic elastomers, and arbitrary combinations thereof. Further, PET, PBT, PCGT, or the like can be used. Among these materials, particularly, polyvinyl chloride is preferably used. Such material having high gas permeability is preferable for a container for storing platelets to improve shelf life of platelets. Therefore, polyolefin or DnDp-plasticized polyvinyl chloride may preferably be used for such material or a material formed in a thin sheet may preferably be used.

Figure 15:
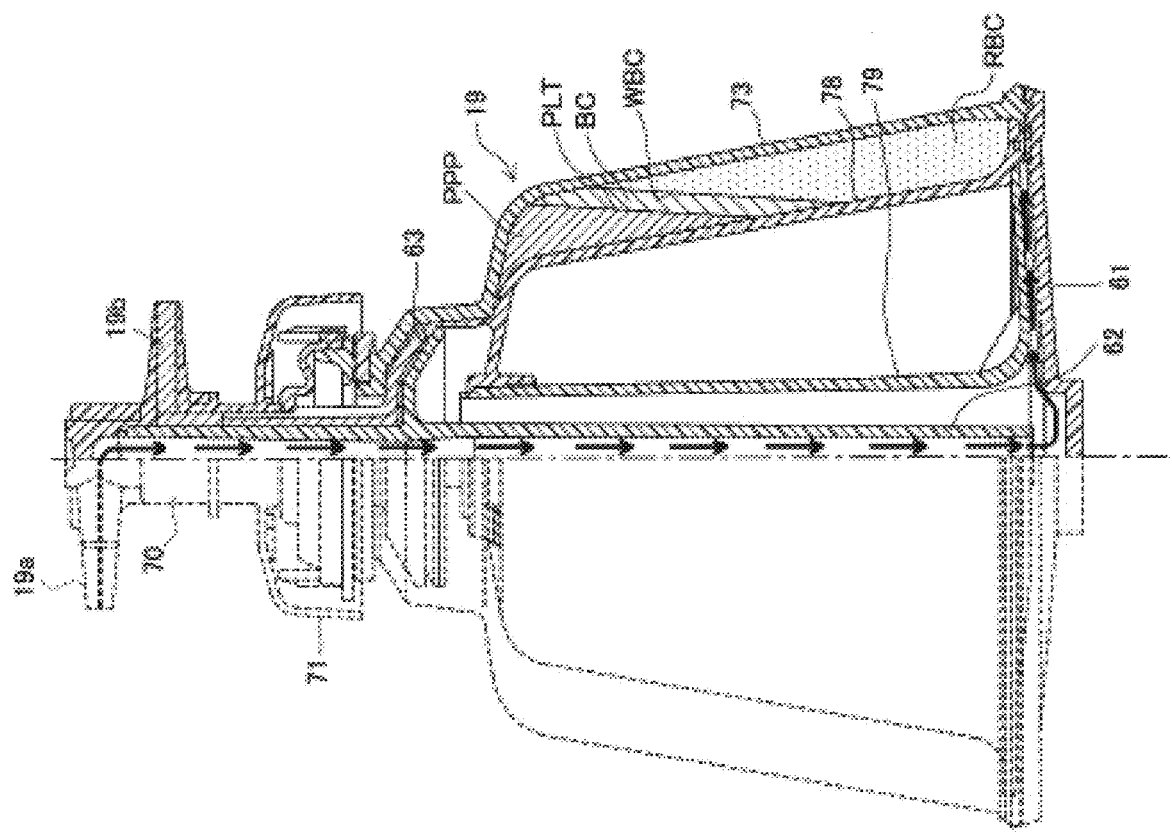
FIG. 15 illustrates a structure of a centrifuge bowl.

The centrifuge bowl will be described referring to FIG. 15. FIG. 15 illustrates a structure of a centrifuge bowl. In FIG. 15, the figure is divided by the center line, where the right hand side illustrates a cross sectional view and the left hand side illustrates an external view in dashed lines.

In the blood component separation device 1, the first port 19a, which is an inflow port, and the second port 19b, which is an outflow port, are formed on the non-rotatable fixed portion 70. A cover 71 and a downwardly extending inflow tube 62 are coupled to the fixed portion 70. By these fixed portions, a side wall 73, an outer shell 78, an inner shell 79, and a bottom plate 61 are integrally and rotatably supported. The bottom plate 61 is coupled to the centrifuge bowl drive unit 15, for example, by suctioning so that the rotational force from the centrifuge bowl drive unit 15 can be transferred to the bottom plate 61. FIG. 15 illustrates a state where whole blood is supplied into the centrifuge bowl 19 from the first port 19a and separated into blood components by centrifugal force.

The centrifugal force produces layers of blood components in the space between the outer shell 78 and the side wall 73. These layers are, from outer side to inner side, in the descending order of specific gravity, a red blood cell layer RBC, a white blood cell layer WBC, a buffy coat layer BC, a platelet layer PLT, and a plasma layer PPP. It is difficult to separate the white blood cell layer WBC and the platelet layer PLT because values of specific gravity are close. Thus, the buffy coat layer BC including the white blood cell layer WBC and the platelet layer PLT exists. Typically, whole blood includes about 55% of plasma PPP, about 43.2% of red blood cells RBC, about 1.35% of white blood cells WBC, and 0.45% of platelets PLT. The centrifuge bowl 19 has an outflow passage 63 in the inner periphery formed somewhat above the middle point of the inflow tube 62. So that the plasma layer PPP formed in the inner side of the space formed by the outer shell 78 and the side wall 73 first flows out from the centrifuge bowl 19 by passing through the outflow port 19b.

Figure 16:
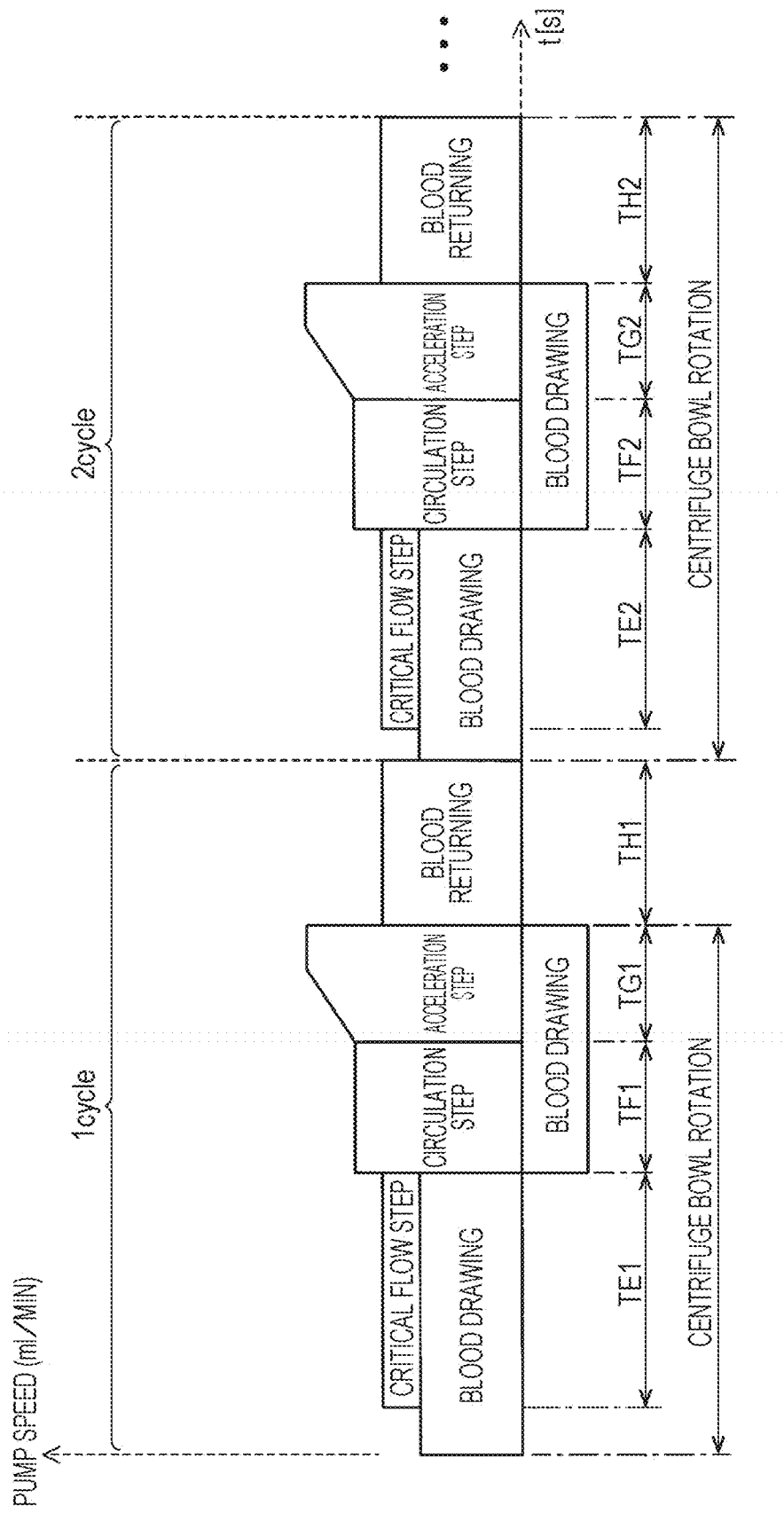
FIG. 16 illustrates operation of the blood component separation device in chronological order.

The operation of the blood component separation device 1 configured as described above is shown in a flowchart in FIG. 18. FIGS. 3 to 14 illustrate operations and steps of the blood component separation device 1. The object of the device is to collect high-concentration platelet liquid. FIG. 16 illustrates an operation chart showing the operation of the blood component separation device 1 in chronological order. FIG. 3 illustrates a first step. The pump outlined with a white inside shows that the pump is operating. The pump outlined with a black inside shows that the pump is not operating. The open/close valve outlined with a white inside shows that the valve is open. The open/close valve outlined with a black inside shows that the valve is closed.

Figure 18:
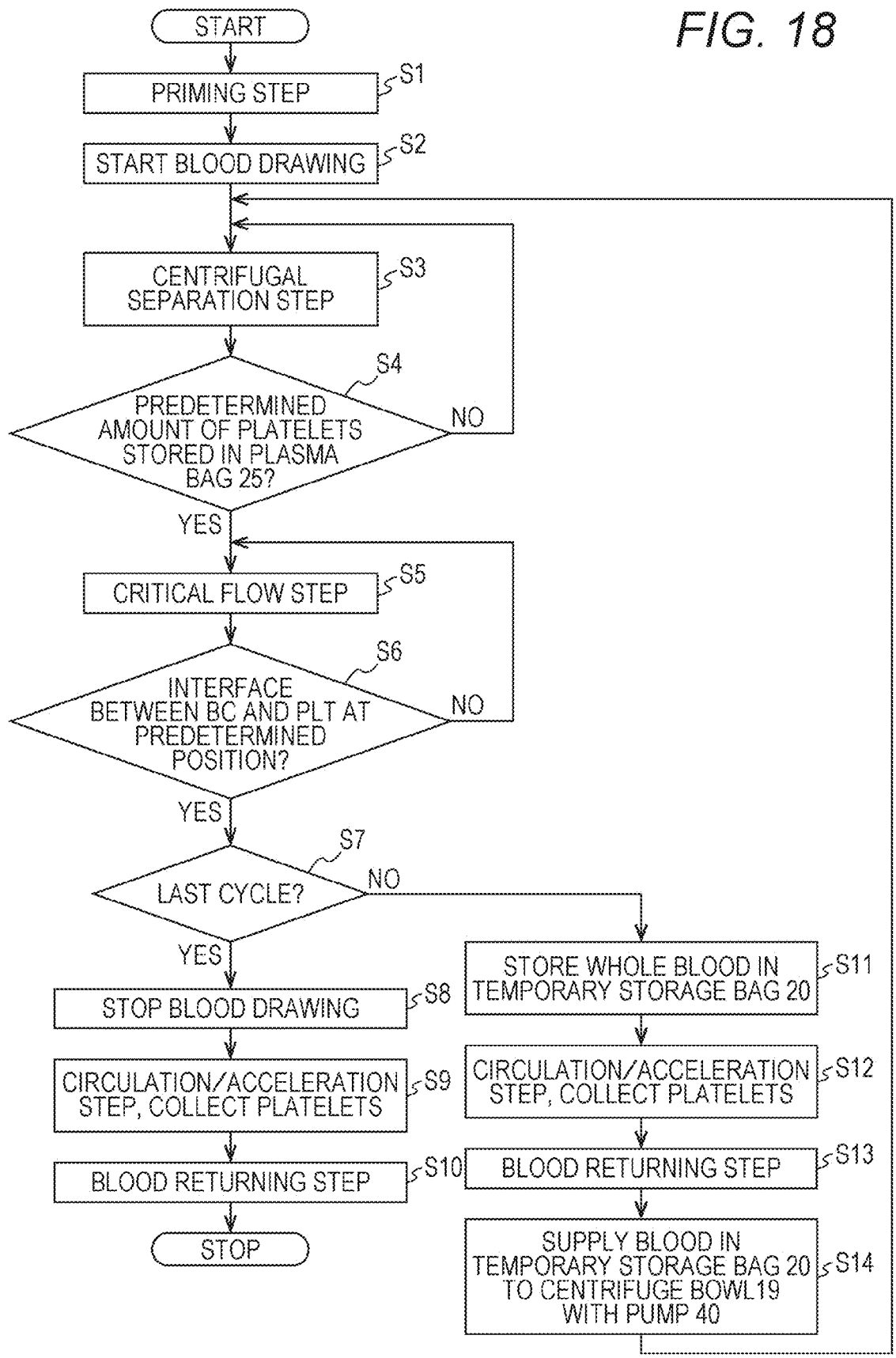
FIG. 18 is a flowchart showing the operation of the blood component separation device.

First, a priming step (S1) illustrated in FIG. 18 is performed. The ACD pump 36 and the first blood pump 13 are driven to supply ACD liquid which prevents blood coagulation to the centrifuge bowl 19 via the opened first open/close valve 16, thereby performing the priming step (first step) of the centrifuge bowl 19, the first blood pump 13, etc. The priming step is performed to previously apply ACD liquid on portions in the donor tube 12, the first blood pump 13, the centrifuge bowl 19, etc., which are to make contact with blood, so that the blood will not coagulate when introduced. From the priming step, the centrifuge bowl drive unit 15 rotates the centrifuge bowl 19 at a predetermined rotational speed.

When the priming step (S1) is finished, the blood drawing needle 11 pierces a donor to start drawing of whole blood (S2). When the blood drawing needle 11 has pierced the donor, first, the initial blood flow is collected in the initial blood flow collecting bag 82 provided in the initial blood flow collecting circuit. The branch 87 provided on the donor tube 12 is initially configured to couple the blood drawing needle 11 and the initial blood flow collecting line 88. When a predetermined amount of blood is stored in the initial blood flow collecting bag, the initial blood flow line 88 is choked by the klemme 90 to secure a flow passage, in the side of the first blood pump 13, of the donor tube 12.

The ACD pump 36 is driven again to supply ACD liquid to the donor tube 12 so as to be mixed with the whole blood which is supplied to the centrifuge bowl 19. When whole blood is supplied to the rotating centrifuge bowl 19, as illustrated in FIG. 3, the air (shown in dashed lines) inside the centrifuge bowl 19 is pushed by the plasma to flow out from the outflow passage 63 located in the inner periphery of the centrifuge bowl 19. The air flows through the opened fifth open/close valve 26 and is stored in the air bag 28. In the centrifuge bowl 19, as illustrated in FIG. 15, the supplied whole blood is separated into components by the centrifugal force produced in the bowl.

Figure 4:
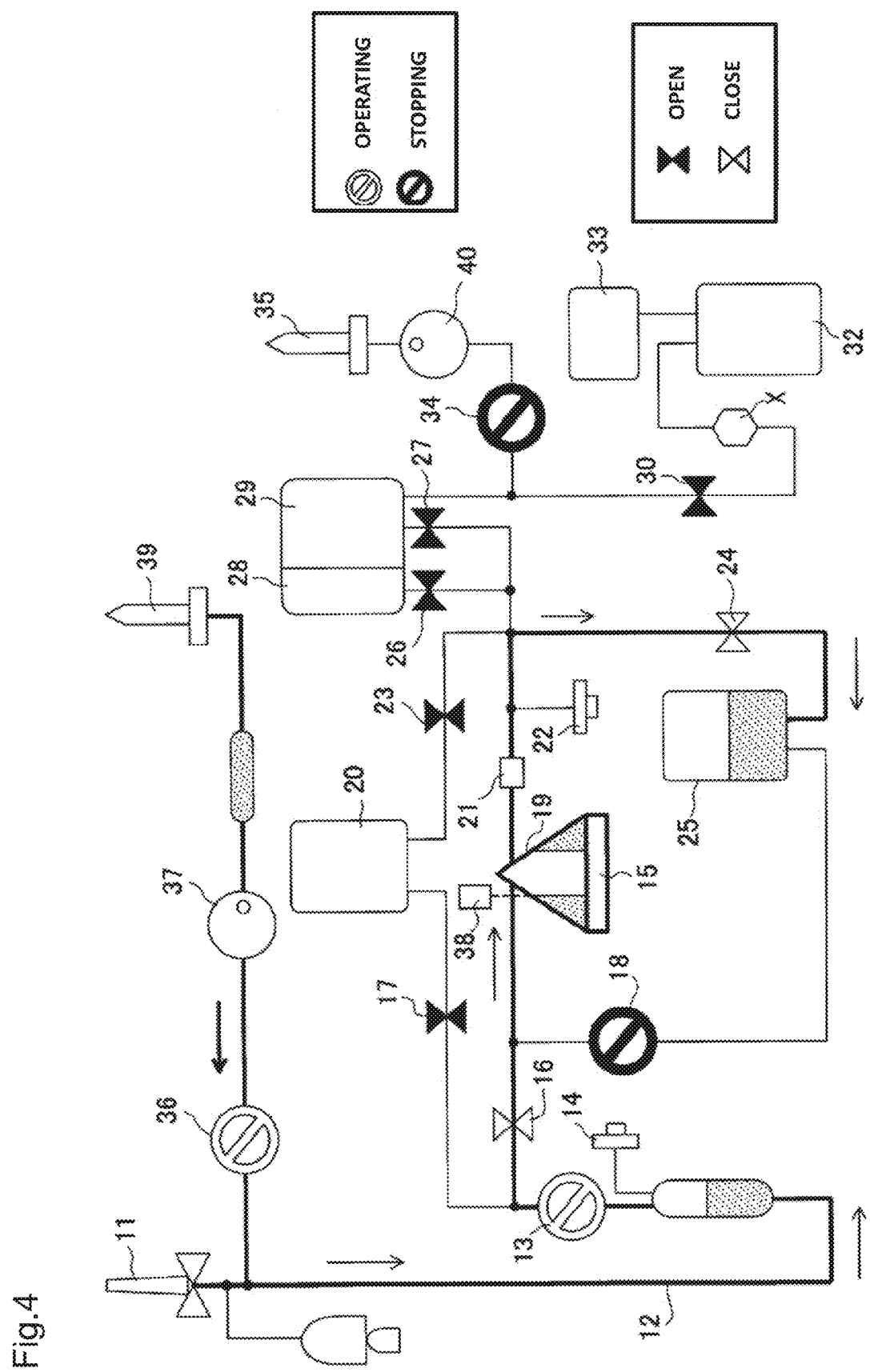
FIG. 4 is a drawing for explaining a second step.

Then when the turbidity sensor 21 detects that the fluid flowing in the tube has changed from air to plasma, the fifth open/close valve 26 is closed and the fourth open/close valve 24 is opened to store plasma spilled out from the centrifuge bowl 19 in the plasma bag 25, as illustrated in FIG. 4. Thus the centrifugal separation step (S3) is performed. As illustrated in FIG. 15, only plasma comes out first from the centrifuge bowl 19.

Figure 5:
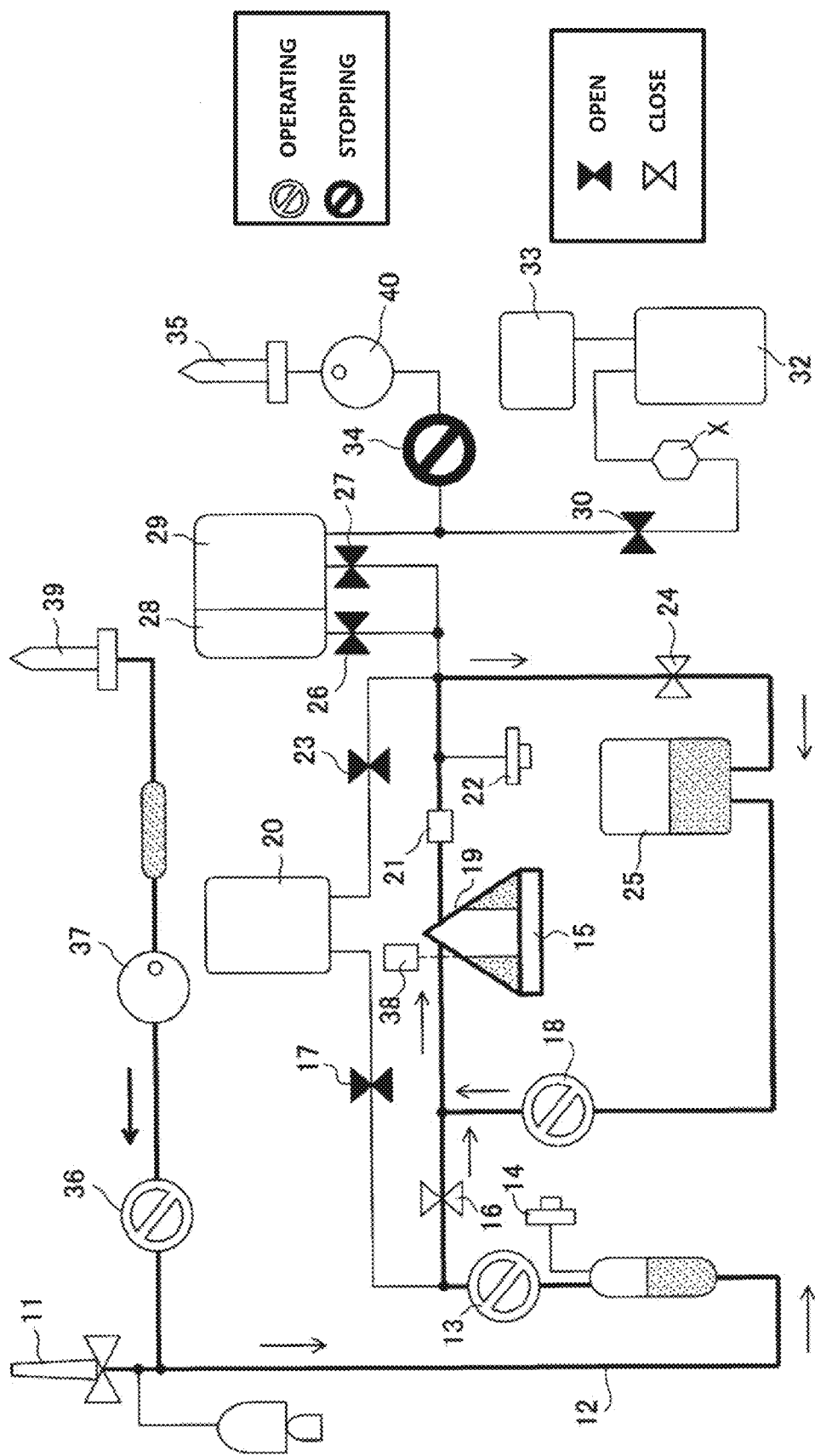
FIG. 5 is a drawing for explaining a third step (critical flow step).

Then when a certain amount of plasma (30 ml for the working example) is stored in the plasma bag 25 (S4: YES), the second blood pump 18 is driven to draw whole blood from the donor, mix the whole blood with the plasma stored in the plasma bag 25, and supply the mixed whole blood and plasma to the centrifuge bowl 19, as illustrated in FIG. 5 (S5). Thus, a third step (critical flow step) is performed. These are performed in a critical flow period TE shown in FIG. 16.

Figure 6:
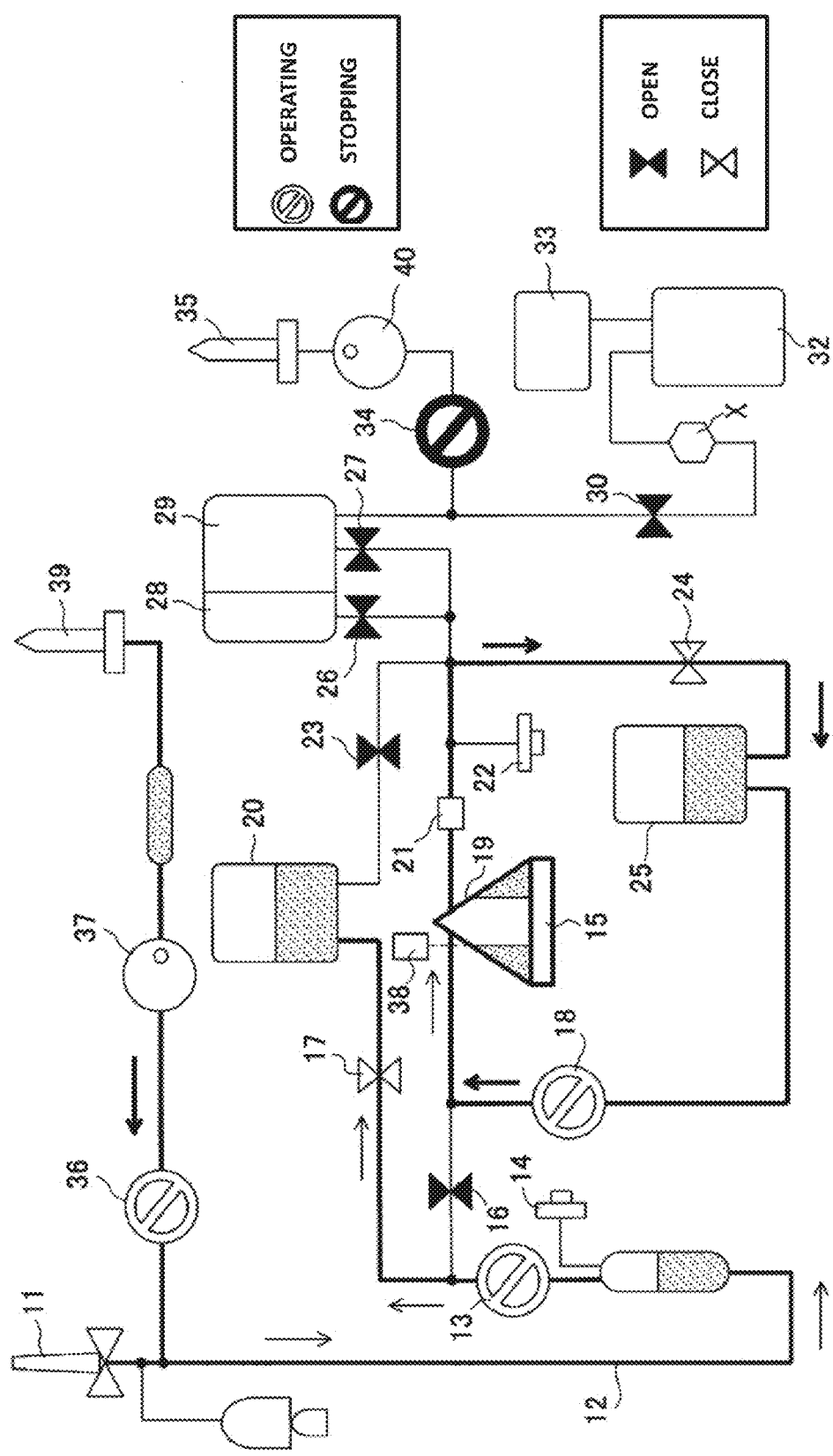
FIG. 6 is a drawing for explaining a fourth step (circulation flow step).

Then, when the interface sensor 38 detects that the interface between the buffy coat BC and the red blood cell RBC in FIG. 15 has come to a predetermined position (S6: YES), the first open/close valve 16 is closed with the second blood pump 18 driving as illustrated in FIG. 6. The plasma in the plasma bag 25 then flows through the second blood pump 18, the centrifugal separator 19, and the fourth open/close valve 24 to return back to the plasma bag 25, thereby performing a circulation step (fourth step) in the circulation/acceleration step. This is performed in a circulation period TF shown in FIG. 16.

At the same time, whether the present cycle is the last cycle is determined. When the present cycle is not the last cycle (S7: NO), the second open/close valve 17 is opened with the first blood pump 13 kept driving to store the drawn whole blood in the temporary storage bag 20 (S11). In other words, whole blood is kept drawn by storing the drawn whole blood in the temporary storage bag 20. Drawing of whole blood is continued until completion of the circulation/acceleration step or reaching a previously determined time or amount of drawing. In the last cycle (S7: YES), the first blood pump 13 is stopped to stop blood drawing (S8).

In the circulation step in the circulation/acceleration step of the working example, the circulation speed is set faster than the critical flow step so as that the plasma circulates with the speed of 100 ml/min, flowing through the centrifuge bowl 19 within 30 to 40 seconds. In this manner, the concentration of particulates in the buffy coat layer BC in FIG. 15 decreases, whereby the white blood cell layer WBC having a larger specific gravity than platelets deposits in the outer side of the buffy coat layer BC. That is, the platelet layer PLT and the white blood cell layer WBC can further distinctly be separated.

Figure 7:
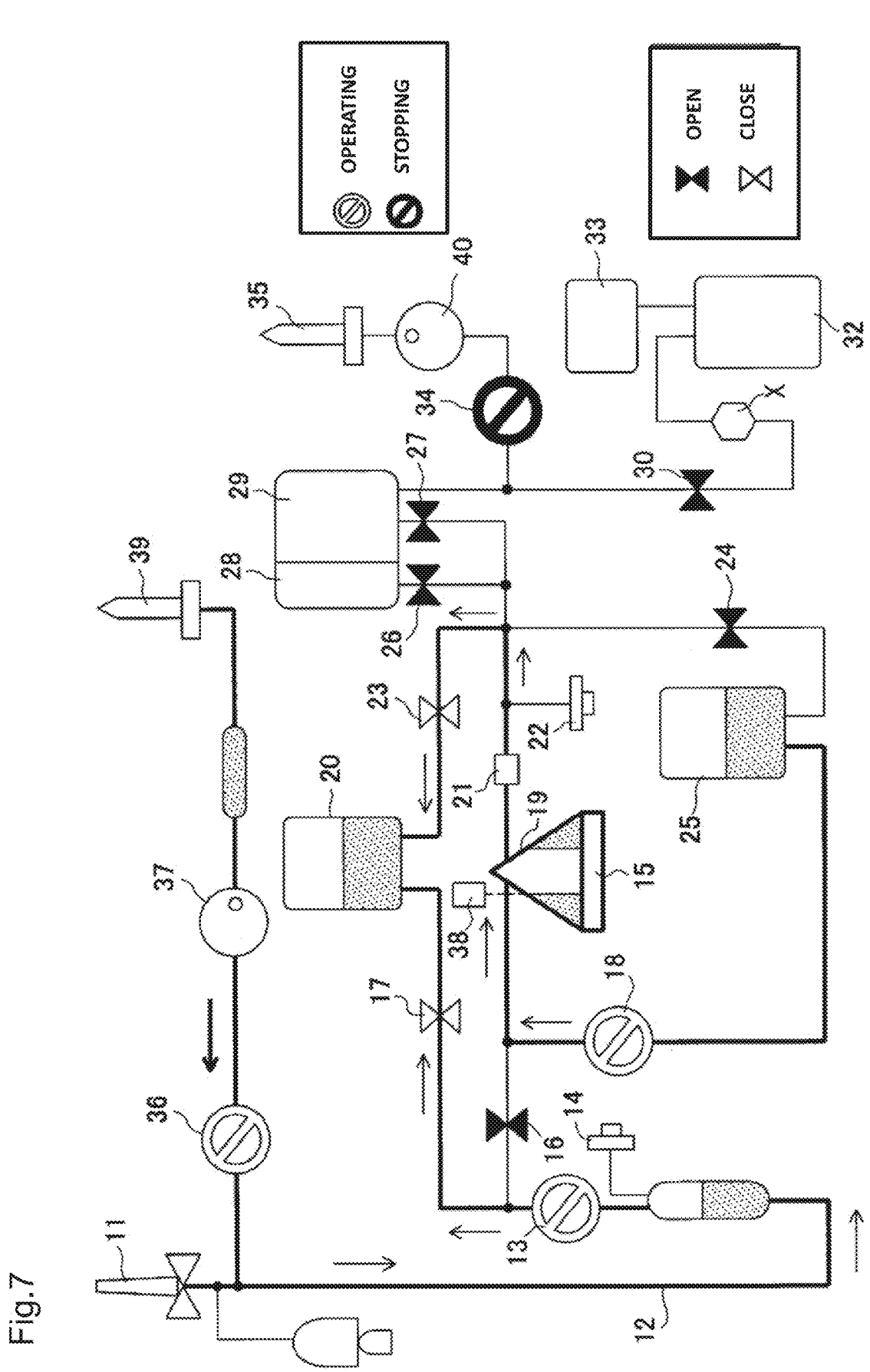
FIG. 7 is a drawing for explaining a step for recovering low-concentration platelet liquid in a fifth step (acceleration step).

Then, after the circulation step is performed for a certain time period, an acceleration step (fifth step) in the circulation/acceleration step is performed as illustrated in FIG. 7. In the acceleration step, by controlling the rotational speed of the second blood pump 18, the rotational speed is gradually raised to gradually increase the flow rate of plasma. In the working example, the flow rate starts from 100 ml/min and is raised to accelerate the flow rate of plasma until platelets flows out. This is performed in an acceleration period TG shown in FIG. 16. FIG. 18 describes the circulation step and the acceleration step together as the circulation/acceleration step (S9). In the acceleration step, the platelets PLT receive ascending force and thereby flows out of the centrifuge bowl 19 from the outflow passage 63, as can be understood in FIG. 15. During this acceleration, the white blood cell layer WBC and the red blood cell layer RBC having large specific gravities, therefore receiving greater effect of centrifugal force, will not flow out from the outflow passage 63.

Figure 17:
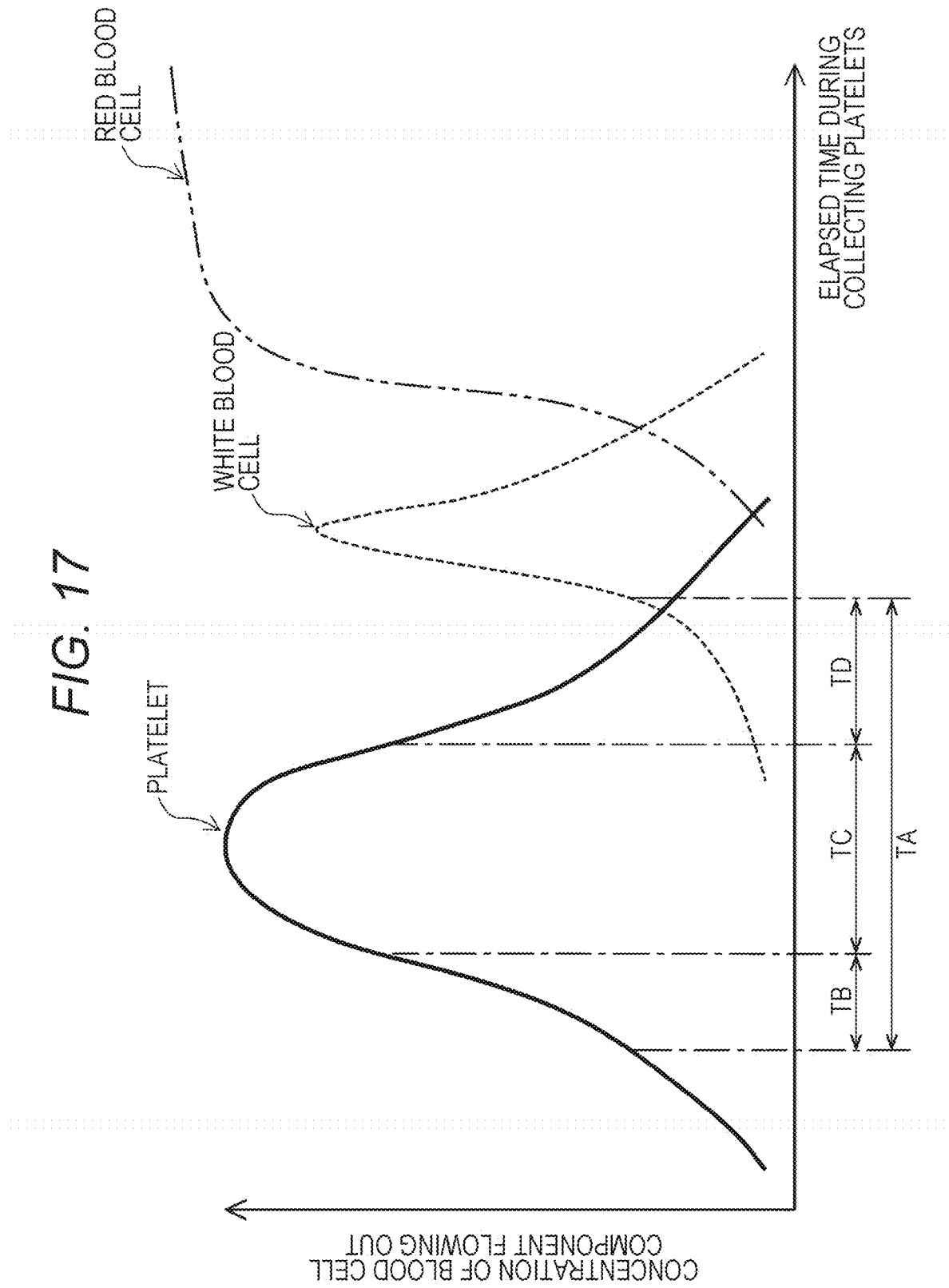
FIG. 17 illustrates change in concentrations of platelets, white blood cells, and red blood cells flowing out.

FIG. 17 illustrates change in concentrations of platelets, white blood cells, and red blood cells flowing out. The horizontal axis represents elapsed time during collecting platelets, and the vertical axis represents concentrations of blood cell components flowing out. First, platelets flow out (outflow period TA). In this period, the outflow rate of platelets gradually increases, and after peaking at the maximum flow rate, the outflow rate gradually decreases. Similarly, the outflow rate of white blood cells gradually increases, and after peaking at the maximum flow rate, the outflow rate gradually decreases.

Figure 19:
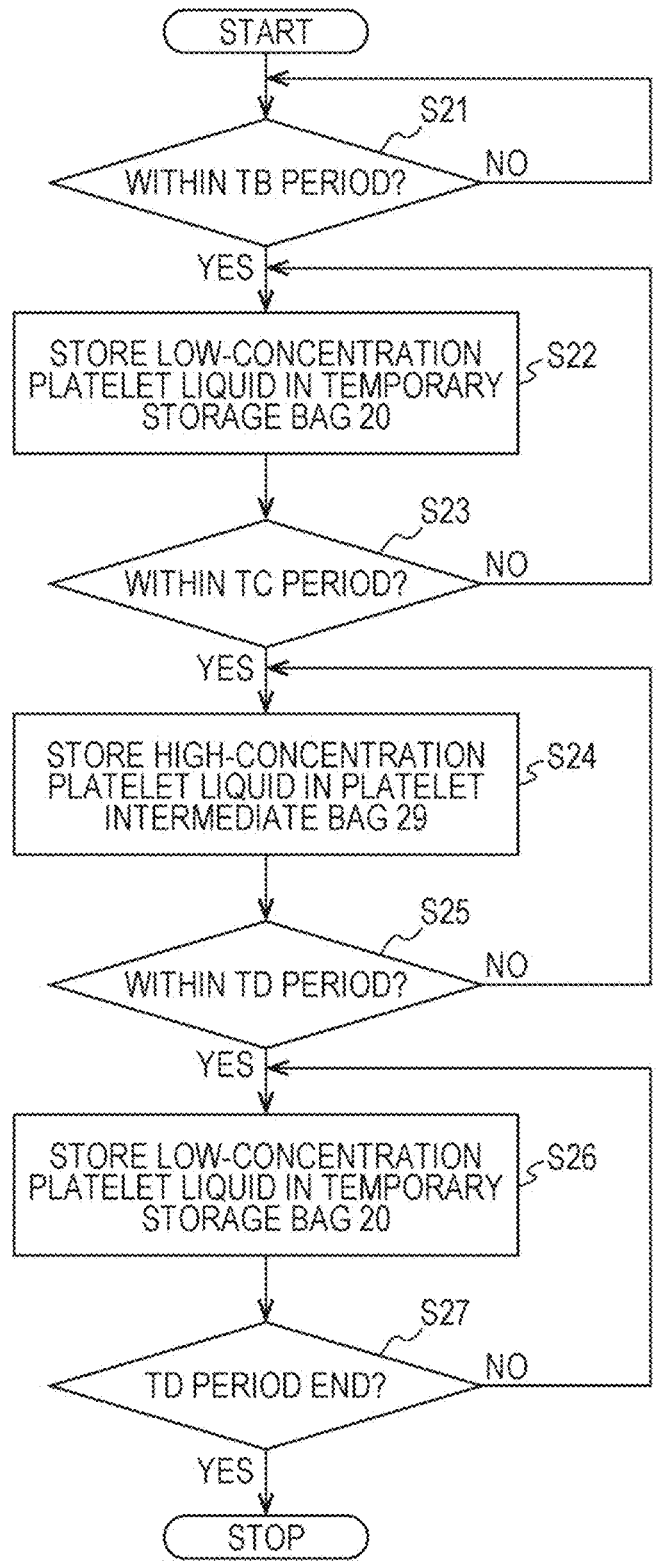
FIG. 19 is a flowchart showing operation performed in the collecting step of platelet liquid.

FIG. 19 illustrates S9 in detail in a flowchart showing the operation of the blood component separation device 1. The outflow period TA of platelets can be divided in three periods, that is, a low-concentration period TB where low-concentration platelet liquid flows out at first, a high-concentration period TC, following the TB period, where high-concentration platelet liquid flows out, and a low-concentration period TD, following the TC period, where low-concentration platelet liquid flows out again. Low-concentration platelet liquid is not necessary for obtaining high-concentration platelet liquid.

In the working example, in the acceleration step as illustrated in FIG. 7, when the turbidity sensor 21 detects platelets, that is, when it is determined that the present period is the TB period (S21: YES), the fourth open/close valve 24 is closed and the third open/close valve 23 is opened to store platelet liquid flowing out during the low-concentration period TB in FIG. 17 in the temporary storage bag 20 (S22). In this state, since the whole blood also flows into the temporary storage bag 20 to be stored, the low-concentration platelet liquid is stored in the temporary storage bag 20 mixed with the whole blood. Also in this state, the first blood pump 13 is kept driving so that the whole blood drawn from the donor is continuously stored in the temporary storage bag 20. Note that, the temporary storage bag 20 is also used as a buffy coat bag as well as a whole blood bag.

Figure 8:
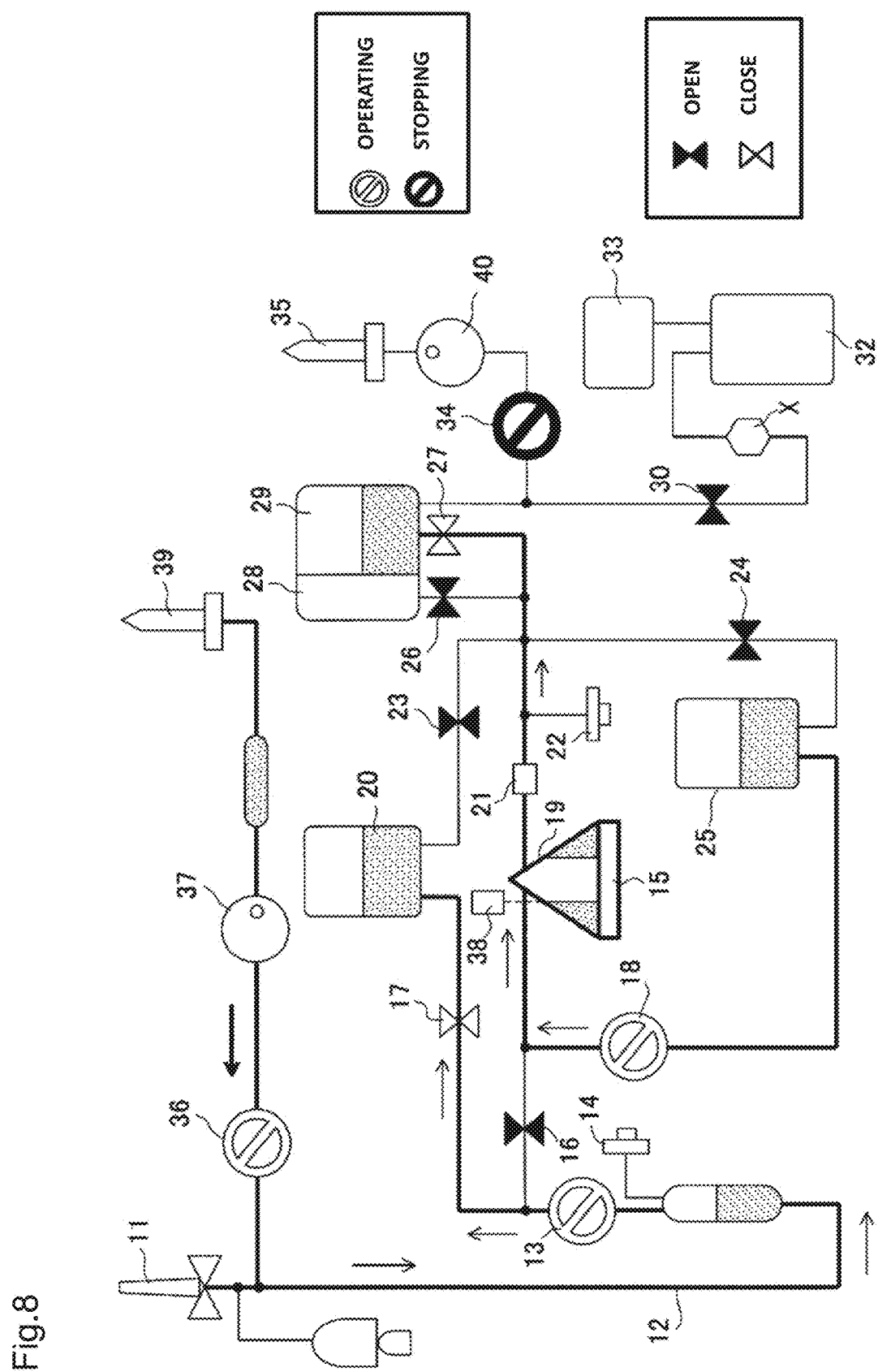
FIG. 8 is a drawing for explaining a step for storing high-concentration platelet liquid in the fifth step (acceleration step).

When the turbidity sensor 21 detects that the concentration of platelet liquid is high, it is determined that the present period is the TC period (S23: YES), and the third open/close valve 23 is closed and the sixth open/close valve 27 is opened as illustrated in FIG. 8. In this manner, the high-concentration platelet liquid flowing out during the high-concentration period TC can be stored in the platelet intermediate bag 29 (S24). If the present cycle is not the last cycle (S7: NO), the first blood pump 13 is kept driving so that the whole blood drawn from the donor is continuously stored in the temporary storage bag 20.

Figure 9:
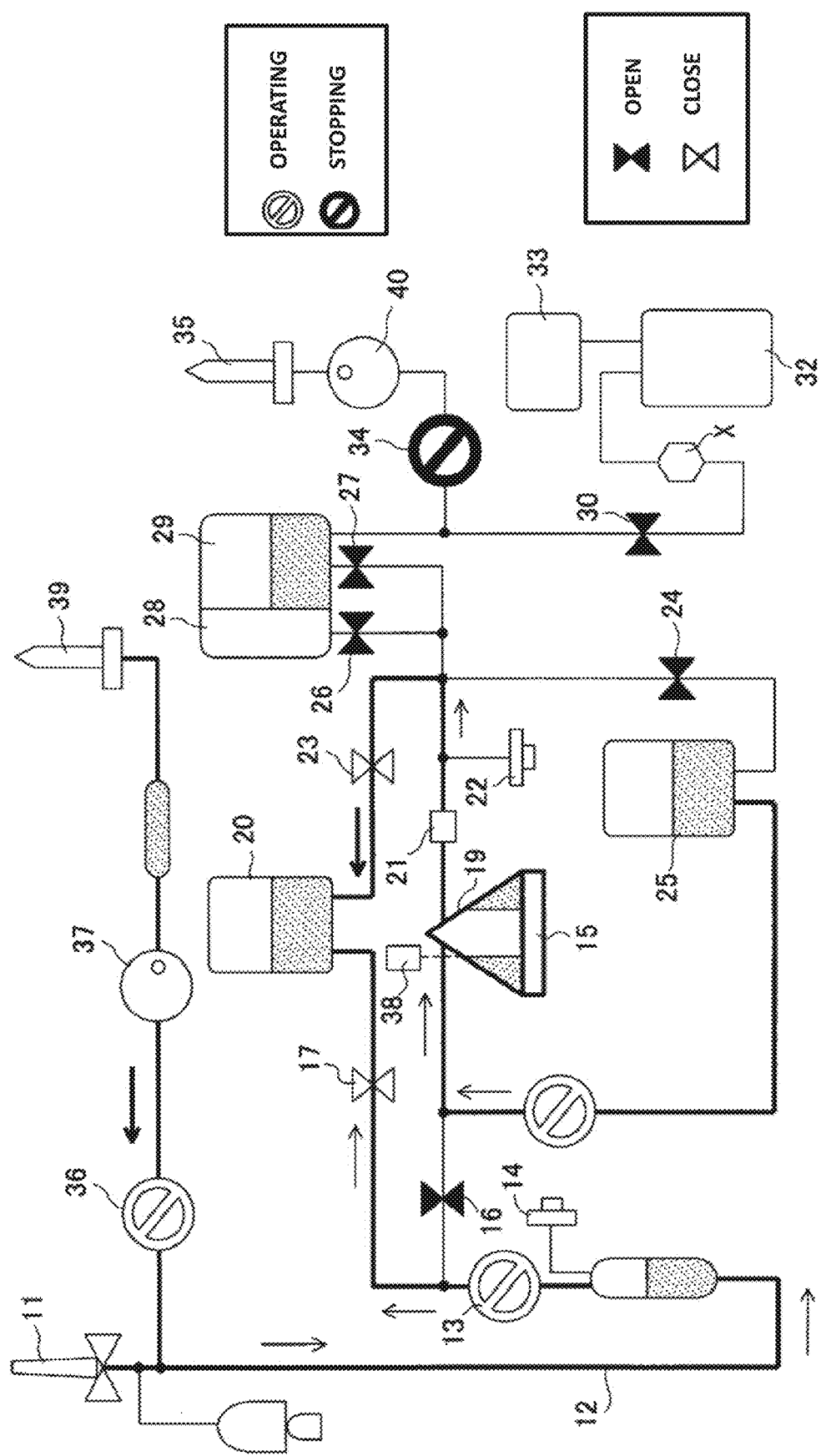
FIG. 9 is a drawing for explaining a step for recovering low-concentration platelet liquid in the fifth step (acceleration step).
Figure 10:
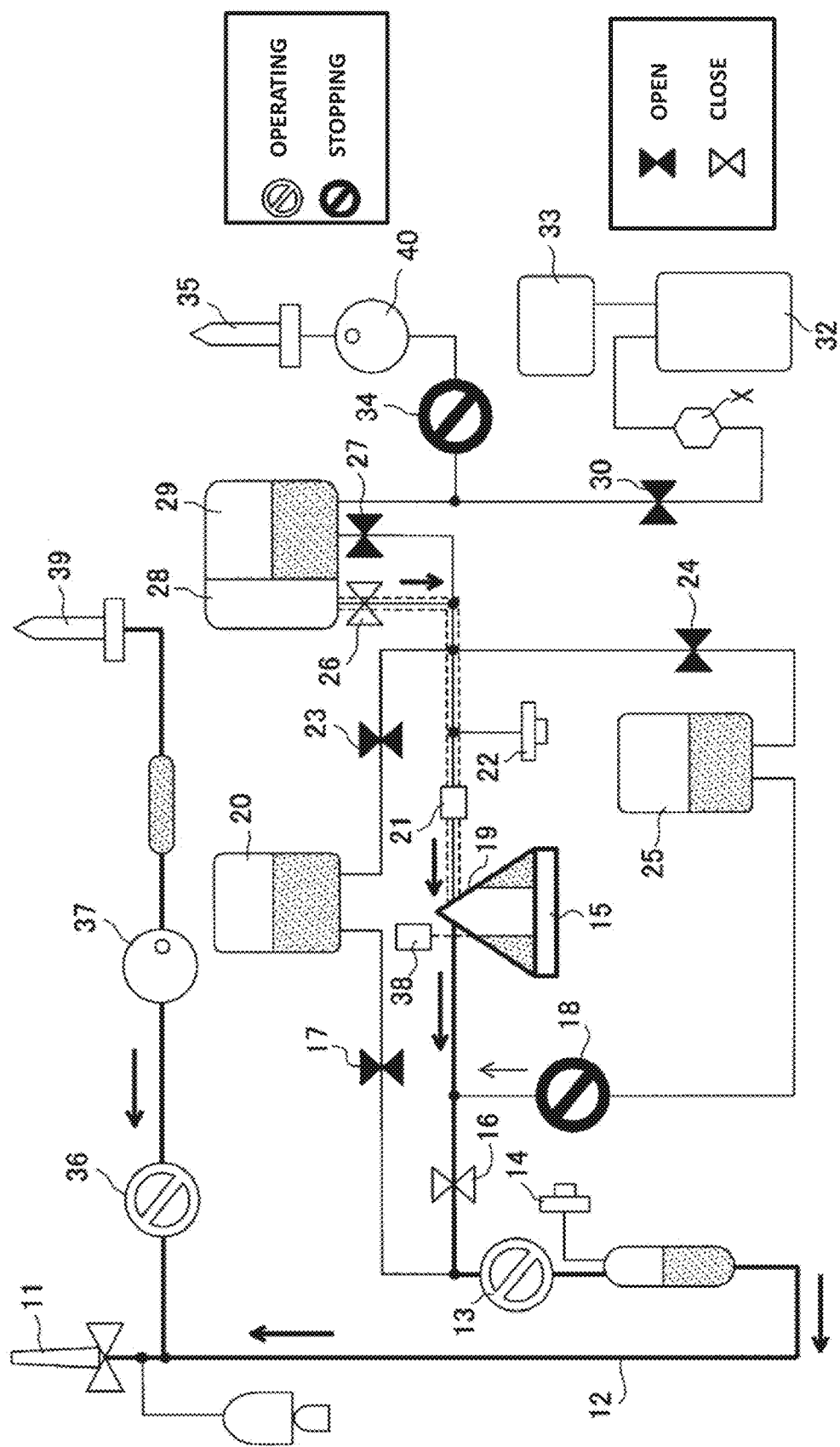
FIG. 10 is a drawing for explaining a blood returning step.

When a predetermined amount of high-concentration platelet liquid is stored in the platelet intermediate bag 29, it is determined that the present period is the TD period (S25: YES), and the sixth open/close valve 27 is closed and the third open/close valve 23 is opened as illustrated in FIG. 9. In this manner, the low-concentration platelet liquid flowing out during the low-concentration period TD can be stored again in the temporary storage bag 20 (S26). If the present cycle is not the last cycle (S7: NO), the first blood pump 13 is kept driving so that the whole blood drawn from the donor is continuously stored in the temporary storage bag 20.

The amount of the high-concentration platelet liquid stored in the platelet intermediate bag 29 can easily be adjusted by controlling the time period in which the sixth open/close valve 27 is opened based on the flow rate of the platelet liquid flowing out from the centrifuge bowl 19. Note that, detail on the amount of high-concentration platelet liquid to be collected in each cycle will be described later.

Now, when a predetermined amount of platelet liquid is collected, in other words, when a predetermined period of time has elapsed after opening the sixth open/close valve 27, it is determined that the TD period is ended (S27: YES) and outflow of platelets has finished. Then, the step proceeds to a blood returning step illustrated in FIGS. 10 and 18 (S10, S13). In this step, the centrifuge bowl 19 stops rotation, the second open/close valve 17 and the third open/close valve 23 are closed, the first open/close valve 16 and the fifth open/close valve 26 are opened, and the first blood pump 13 is reversely rotated, whereby the blood returning starts to return the blood remaining in the centrifuge bowl 19 to the donor. The first blood pump 13 is reversely operated with double the rotational speed of the normal rotation to shorten the time of blood returning. Further, when required, the second blood pump 18 is driven to return the excessive plasma stored in the plasma bag 25.

Figure 11:
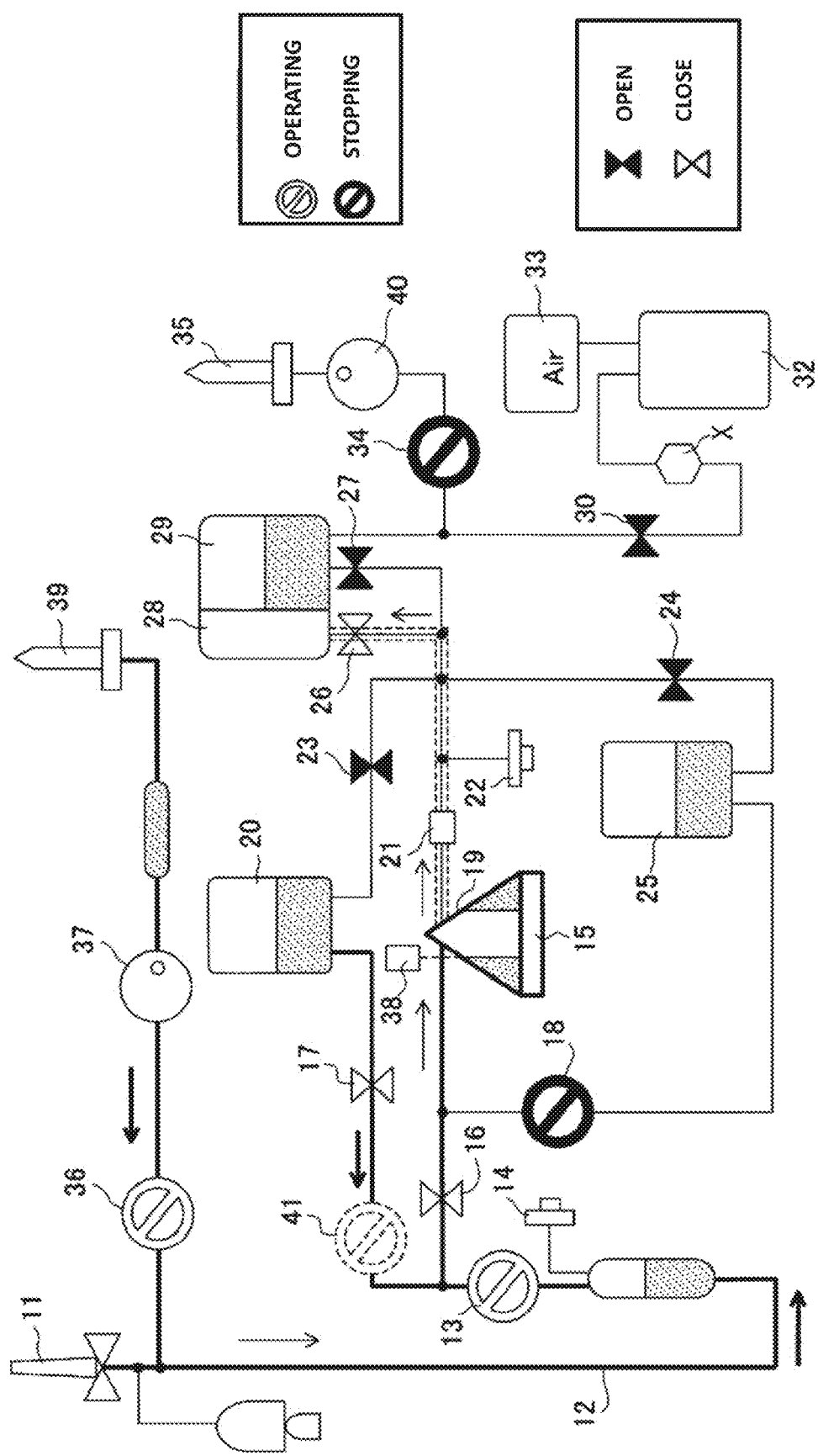
FIG. 11 is a drawing for explaining the second step in a second cycle.

When the blood returning finishes, and if the present cycle is the last cycle (S7: YES), the entire step is finished. When the present cycle is not the last cycle (S7: NO), the centrifuge bowl 19 starts rotating as illustrated in FIG. 11 and the first blood pump 13 starts normal rotation again to perform blood drawing. At the same time, the second open/close valve 17 is opened to allow the blood stored in the temporary storage bag 20 to flow into the centrifuge bowl 19 (S14). The liquid supply from the temporary storage bag 20 may be performed by difference in elevation or by providing a blood pump 41 (illustrated in a dashed line) between the second open/close valve 17 and the first open/close valve 16 as illustrated in FIG. 11.

Figure 12:
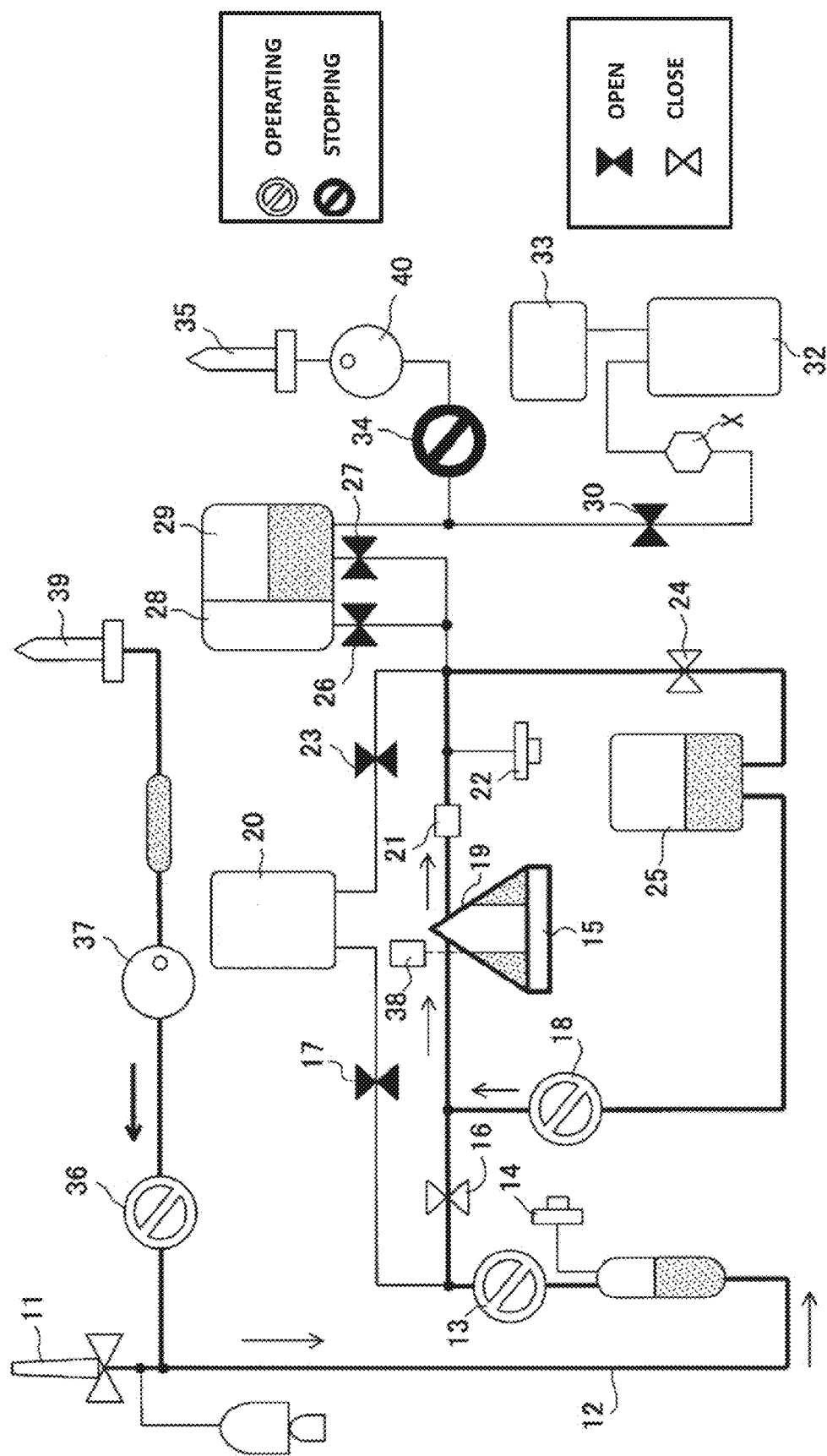
FIG. 12 is a drawing for explaining the second step in a third cycle.

Then, when it is confirmed that all the blood in the temporary storage bag 20 has returned to the centrifuge bowl 19 and that a predetermined amount of plasma is stored in the plasma bag 25 (S4: YES), as illustrated in FIG. 12 (state same as in FIG. 5), the second open/close valve 17 is closed and the second blood pump 18 is driven to start the critical flow step of plasma, followed by the step in FIG. 6 (circulation step). This cycle is repeated, typically three or four times, until a predetermined amount of platelets PLT is obtained. In the embodiment, this cycle is performed four times to obtain a predetermined amount (100 ml in the embodiment) of concentrated platelets.

When the operation finishes with three cycles, blood drawing is performed in parallel in a circulation period TF2 and an acceleration period TG2 in the second cycle to store whole blood in the temporary storage bag 20. Then during blood drawing in the third cycle, the blood in the temporary storage bag 20 is mixed with whole blood and supplied to the centrifuge bowl 19. Further, in a circulation period TF3 and an acceleration period TG3 in the third cycle, blood drawing is not performed. This is because the fourth cycle will not be performed. When the operation finishes with three cycles, the blood drawing needle 11 is removed from the donor after blood returning in the third cycle finishes, and the blood drawing finishes.

Now, the amount of high-concentration platelet liquid to be collected in the platelet intermediate bag 29 in each cycle will be described. As illustrated in FIG. 20, the amount of high-concentration platelet liquid to be collected in the last cycle (fourth cycle in the embodiment) is set to be greater than the amount of high-concentration platelet liquid to be collected in each of other cycles (first to third cycles in the embodiment). That is, the amount of high-concentration platelet liquid collected in the first cycle is set to be the smallest among all the cycles, and the amount of high-concentration platelet liquid collected in the final fourth cycle is set to be the greatest among all the cycles.

Specifically, in Working Example 1, for example, the amount of platelet liquid to be collected may be 20 ml for the first cycle, 20 ml for the second cycle, 20 ml for the third cycle, and 40 ml for the fourth cycle, that is, total of 100 ml. Further, in Working Example 2, the amount of platelet liquid to be collected can be 20 ml for the first cycle, 24 ml for the second cycle, 28 ml for the third cycle, and 28 ml for the fourth cycle, that is, total of 100 ml. Further, in Working Example 3, the amount of platelet liquid to be collected can be 20 ml for the first cycle, 22 ml for the second cycle, 26 ml for the third cycle, and 32 ml for the fourth cycle, that is, total of 100 ml.

The minimum amount to be collected that is set for the first cycle may be same as the amount set for other cycles (as in Working Example 1). Similarly, the maximum amount to be collected that is set for the fourth cycle may be same as the amount set for other cycles (as in Working Example 2).

In this manner, from the second cycle onward, since the low-concentration platelet liquid stored in the temporary storage bag 20 in the immediately preceding cycle is mixed with whole blood to be supplied to the centrifuge bowl 19, the concentration of platelets in the centrifuge bowl 19 in the fourth cycle is the highest. Therefore, greater amount of platelets can be collected for the same target amount of high-concentration platelet liquid to be collected compared with conventional devices. That is, greater amount of platelets can efficiently be collected.

Even when the operation finishes with three cycles, the amount of high-concentration platelet liquid to be collected in each cycle may be set in a similar manner to the case when the operation finishes with four cycles as described above.

As in Working Examples 2 and 3, by varying the amount of high-concentration platelet liquid to be collected in the platelet intermediate bag 29 in each cycle so as not to be smaller than the amount of high-concentration platelet liquid collected in the preceding cycle, high-concentration platelet liquid can efficiently be collected not only in the fourth cycle but also in the second and third cycles. Thus, further greater amount of platelets can efficiently be collected.

Figure 13:
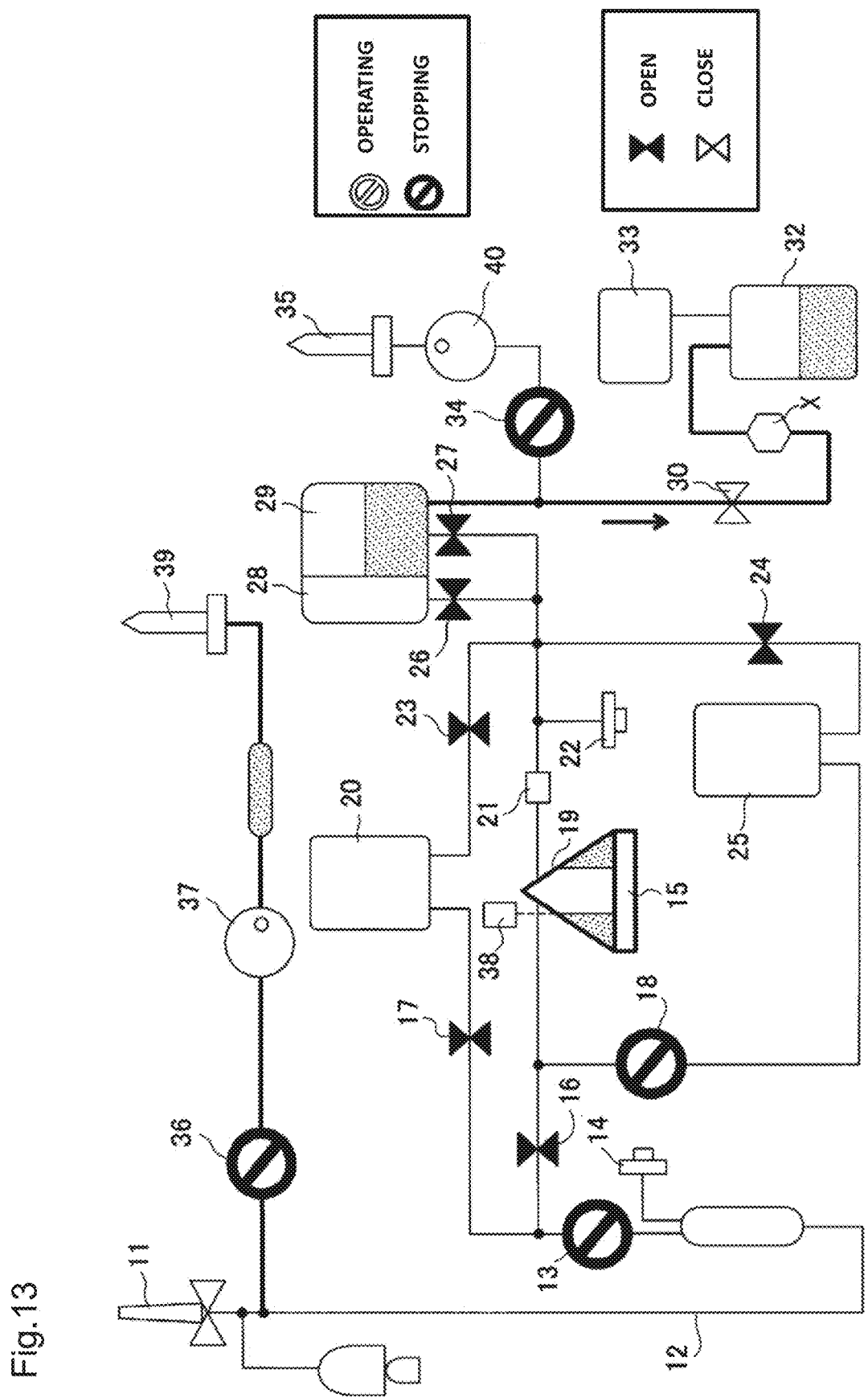
FIG. 13 is a drawing for explaining a processing step of platelet liquid.

Then, the third blood pump 34 is driven to inject a suitable amount of platelet reserve liquid into the platelet intermediate bag 29 from a bottle needle 35 coupled to the platelet reserve liquid bottle. Further, as illustrated in FIG. 13, the seventh open/close valve 30 is opened to inject high-concentration platelet liquid and platelet reserve liquid stored by a certain amount (for example, 100 ml in the embodiment) in the platelet intermediate bag 29 into the platelet bag 32 through the white blood cell removal filter X. In this process, the air in the platelet bag 32 moves into the air bag 33.

Figure 14:
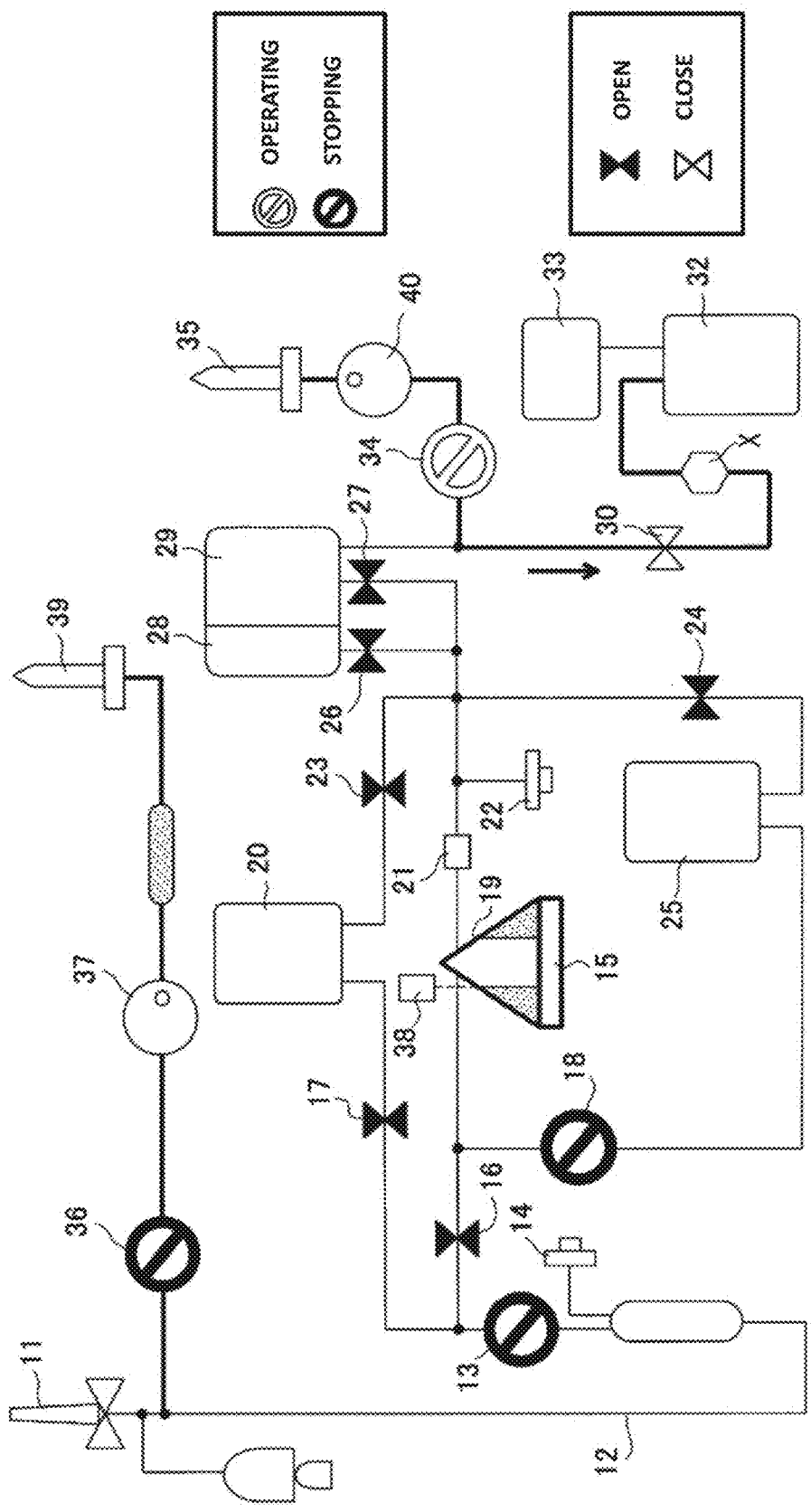
FIG. 14 is a drawing for explaining a final processing step of platelet liquid.

After confirming that the high-concentration platelet liquid stored in the platelet intermediate bag 29 has completely been taken out, the third blood pump 34 is driven to inject the platelet reserve liquid remaining in the platelet reserve liquid bottle into the platelet bag 32, through the sterilizing filter 40 and the white blood cell removal filter X, from the bottle needle 35 coupled to the platelet reserve liquid bottle, as illustrated in FIG. 14. In this manner, the high-concentration platelet liquid which is already filtered and remaining on the white blood cell removal filter X is recovered. Then, two tubes of the platelet bag is sealed. In this manner, the platelet bag 32 storing high-concentration platelet liquid is provided.

As described above in detail, in the blood component separation device 1 according to the embodiment, the amount of high-concentration platelet liquid to be collected in the platelet intermediate bag 29 in each cycle is varied so that the amount of high-concentration platelet liquid to be collected in the last cycle (fourth cycle in the embodiment) is set to be greater than the amount of high-concentration platelet liquid to be collected in each of other cycles (first to third cycles in the embodiment). Further, from the second cycle onward, concentration of platelets in the centrifuge bowl 19 increases and become maximum in the fourth cycle. Therefore, greater amount of platelets can be collected for the same target amount of high-concentration platelet liquid to be collected compared with conventional devices. That is, greater amount of platelets can efficiently be collected.

The embodiment described above is merely an example and does not limit the present invention. It goes without saying that various improvements and modifications can be made without departing from the spirit and the scope of the present invention. For example, in the embodiment described above, drawing of whole blood is performed in parallel with the circulation flow step and the acceleration step. However, a switching unit may be provided in the blood component separation device to perform drawing of whole blood not in parallel, as is performed in conventional technique.

Further, in the embodiment described above, the temporary storage bag 20 is used as a buffy coat bag as well as a whole blood bag. However, the buffy coat bag and the whole blood bag may separately be provided in parallel.

REFERENCE SIGNS LIST 1 blood component separation device
2 controller
10 blood component separation circuit
13a first port
13b second port
15 centrifuge bowl drive unit
19 centrifuge bowl
20 temporary storage bag
21 turbidity sensor
25 plasma bag
28 air bag
29 platelet intermediate bag
32 platelet bag
33 air bag
38 interface sensor
PLT platelet
WBC white blood cell
BC buffy coat
RBC red blood cell

The invention claimed is:

1. A method for controlling a blood component separation device comprising:
a centrifugal separator configured to separate a predetermined blood component from whole blood into a plurality of blood components; and
a container for containing the predetermined blood component centrifugally separated,
wherein the blood component separation device is configured to perform at least the following steps
(a) centrifugal separation step for introducing whole blood drawn from a donor into the centrifugal separator to separate whole blood into a plurality of blood components,
(b) circulation flow step for introducing a predetermined first blood component, among centrifugally separated blood components, separated by the centrifugal separation into the centrifugal separator together with whole blood,
(c) circulation/acceleration step, performed after a predetermined amount of the first blood component is separated in the circulation flow step, in which supply of whole blood to the centrifugal separator is stopped to introduce only the first blood component into the centrifugal separator to further circulate the first blood component for a predetermined period of time, and a circulation flow speed is then increased so that a second blood component is separated by the centrifugal separator and collected, and
(d) blood returning step for returning blood components remaining after collecting a predetermined amount of the second blood component in the circulation/acceleration step to the donor,
wherein the circulation/acceleration step includes a first collecting step for transferring a portion of the second blood component with a first concentration to a temporary storage container and
a second collecting step for collecting a portion of the second blood component with a second concentration higher than said first concentration,
wherein the second blood component with first concentration transferred to the temporary storage container is introduced into the centrifugal separator together with whole blood drawn in a following cycle, where the steps (a) to (d) constitute one cycle, and
wherein, as for the second collecting step, an amount of the second blood component with second concentration to be collected in a first cycle is set to be smallest among all cycles, and an amount of the second blood component with second concentration to be collected in a last cycle is set to be greatest among all the cycles.

2. The method for controlling a blood component separation device according to claim 1,
wherein an amount of the second blood component with second concentration to be collected in the second collecting step in each cycle is varied.

3. The method for controlling a blood component separation device according to claim 2,
wherein an amount of the second blood component with second concentration to be collected in the second collecting step in each cycle is varied so as the amount to be collected shall not be smaller than an amount of the second blood component with second concentration to be collected in a preceding cycle.

* * * * *